United States Patent
Piligian et al.

(10) Patent No.: US 9,687,309 B2
(45) Date of Patent: Jun. 27, 2017

(54) EXPANDABLE DEVICES, RAIL SYSTEMS, AND MOTORIZED DEVICES

(71) Applicants: George J. Piligian, New York, NY (US); HooTee Ong, Lexington, MA (US)

(72) Inventors: George J. Piligian, New York, NY (US); HooTee Ong, Lexington, MA (US)

( * ) Notice: Subject to any disclaimer, the term of this patent is extended or adjusted under 35 U.S.C. 154(b) by 0 days.

(21) Appl. No.: 15/140,176

(22) Filed: Apr. 27, 2016

(65) Prior Publication Data

US 2016/0296295 A1   Oct. 13, 2016

Related U.S. Application Data

(63) Continuation of application No. 13/877,660, filed as application No. PCT/US2011/054829 on Oct. 4, 2011, now Pat. No. 9,358,073.

(Continued)

(51) Int. Cl.
*A61B 1/32* (2006.01)
*A61B 17/02* (2006.01)
(Continued)

(52) U.S. Cl.
CPC .......... *A61B 34/30* (2016.02); *A61B 17/0218* (2013.01); *A61B 34/72* (2016.02); *A61M 29/02* (2013.01); *A61B 17/0281* (2013.01); *A61B 18/02* (2013.01); *A61B 18/08* (2013.01); *A61B 18/12* (2013.01); *A61B 18/1442* (2013.01); *A61B 18/1492* (2013.01); *A61B 90/30* (2016.02); *A61B 90/50* (2016.02);
(Continued)

(58) Field of Classification Search
CPC . A61B 17/02; A61B 17/0218; A61B 17/0225; A61B 17/0281; A61B 2017/00902; A61B 2017/00946; A61B 2017/0287; A61B 19/22; A61B 19/2203; A61B 2019/2242; A61B 2019/2249; A61B 1/32
USPC .................................................. 600/201–210
See application file for complete search history.

(56) References Cited

U.S. PATENT DOCUMENTS 3,863,639 A * 2/1975 Kleaveland ........ A61B 17/0293
128/850
4,000,757 A * 1/1977 Freeman ................... F15C 1/08
137/834

(Continued)

*Primary Examiner* — Christian Sevilla
*Assistant Examiner* — Eric S Gibson
(74) *Attorney, Agent, or Firm* — The Fedde Law Firm; Kenton Fedde; Nathaniel Fedde

(57) ABSTRACT

Provided herein are expandable devices, rail systems, and motorized devices. In one embodiment, an expandable device comprises an expandable sac having a tool housed therein. The expandable device is optionally configured for operation while inside a body cavity. The expandable device optionally comprises at least one rail in the sac, and at least one railed device coupled to the rail for movement there on. Movement of the railed device on the rail is provided by, for example, a motor such as an electromagnetic motor or an inch-worm type motor. Expandable devices can be used, for example, to perform minimally invasive medical procedures requiring access to a body cavity. Expandable devices can also be used, for example, to provide safe and stable transport of instruments to the body cavity.

20 Claims, 21 Drawing Sheets

US 9,687,309 B2

Page 2

Related U.S. Application Data

(60) Provisional application No. 61/404,395, filed on Oct. 4, 2010.

(51) Int. Cl.
*A61B 34/30* (2016.01)
*A61M 29/02* (2006.01)
*A61B 34/00* (2016.01)
A61B 18/02 (2006.01)
A61B 18/08 (2006.01)
A61B 18/12 (2006.01)
A61B 18/14 (2006.01)
A61B 17/00 (2006.01)
A61B 18/00 (2006.01)
A61N 7/02 (2006.01)
A61B 90/30 (2016.01)
A61B 90/50 (2016.01)

(52) U.S. Cl.
CPC ........ *A61B 2017/00075* (2013.01); *A61B 2017/00084* (2013.01); *A61B 2017/00318* (2013.01); *A61B 2017/00398* (2013.01); *A61B 2017/00557* (2013.01); *A61B 2017/00818* (2013.01); *A61B 2017/00902* (2013.01); *A61B 2017/00946* (2013.01); *A61B 2017/0225* (2013.01); *A61B 2018/00577* (2013.01); *A61B 2018/141* (2013.01); *A61B 2034/301* (2016.02); *A61B 2034/303* (2016.02); *A61B 2218/001* (2013.01); *A61N 7/02* (2013.01)

(56) References Cited

U.S. PATENT DOCUMENTS

| | | | | |
|---|---|---|---|---|
| 4,157,085 A * | 6/1979 | Austad | ............... | A61F 2/12 128/898 |
| 4,183,102 A * | 1/1980 | Guiset | ............... | A61F 2/82 604/101.01 |
| 4,217,889 A * | 8/1980 | Radovan | ............... | A61F 2/12 600/20 |
| 4,447,227 A * | 5/1984 | Kotsanis | ............ | A61B 17/0218 604/908 |
| 4,501,264 A * | 2/1985 | Rockey | ............... | A61F 5/00 128/898 |
| 4,574,780 A * | 3/1986 | Manders | ............... | A61B 90/02 128/898 |
| 4,615,704 A * | 10/1986 | Frisch | ............... | A61B 90/02 128/899 |
| 4,651,717 A * | 3/1987 | Jakubczak | ............ | A61B 90/02 128/899 |
| 4,666,447 A * | 5/1987 | Smith | ............... | A61B 90/02 128/899 |
| 4,763,653 A * | 8/1988 | Rockey | ............... | A61B 17/12 604/103.07 |
| 4,841,948 A * | 6/1989 | Bauer | ............... | A61B 90/02 128/897 |
| 4,878,495 A * | 11/1989 | Grayzel | ............... | A61M 29/02 604/101.01 |
| 4,976,710 A * | 12/1990 | Mackin | ............ | A61B 1/00082 604/916 |
| 4,984,564 A * | 1/1991 | Yuen | ............... | A61B 17/0293 600/207 |
| 5,109,875 A * | 5/1992 | Gottlieb | ............... | A61B 90/02 128/898 |
| 5,309,896 A * | 5/1994 | Moll | ............ | A61B 17/00234 128/898 |
| 5,331,975 A * | 7/1994 | Bonutti | ............ | A61B 17/0218 128/898 |
| 5,361,752 A * | 11/1994 | Moll | ............... | A61B 17/0218 600/205 |
| 5,450,843 A * | 9/1995 | Moll | ............... | A61B 17/0218 600/207 |
| 5,527,264 A * | 6/1996 | Moll | ............... | A61B 17/0218 600/204 |
| 5,562,603 A * | 10/1996 | Moll | ............... | A61B 17/0218 600/204 |
| 5,571,179 A * | 11/1996 | Manders | ............... | A61B 90/02 128/899 |
| 5,735,791 A * | 4/1998 | Alexander, Jr. | ........ | A61B 17/02 600/207 |
| 5,816,257 A * | 10/1998 | Chin | ............... | A61B 17/00 128/898 |
| 5,836,871 A * | 11/1998 | Wallace | ........... | A61B 17/0218 600/204 |
| 5,865,728 A * | 2/1999 | Moll | ............... | A61B 17/0218 600/204 |
| 6,040,643 A * | 3/2000 | Bruns | ............... | F03G 7/06 310/12.01 |
| 6,099,518 A * | 8/2000 | Adams | ............... | A61B 17/0218 604/264 |
| 7,122,003 B2 * | 10/2006 | Nakao | ............ | A61B 1/00082 600/204 |
| 7,544,213 B2 * | 6/2009 | Adams | ............... | A61F 2/0063 606/151 |
| 8,157,727 B2 * | 4/2012 | Stefanchik | ........ | A61B 1/00135 600/104 |
| 8,814,788 B2 * | 8/2014 | Gan | ............... | A61B 17/0218 600/206 |
| 8,956,286 B2 * | 2/2015 | Shibley | ............... | A61M 13/003 600/235 |
| 8,974,374 B2 * | 3/2015 | Schostek | ........... | A61B 19/2203 600/118 |
| 9,044,210 B1 * | 6/2015 | Hoyte | ............. | A61B 17/00234 |
| 9,060,781 B2 * | 6/2015 | Farritor | ............. | A61B 18/1445 |
| 2003/0233025 A1 * | 12/2003 | Saadat | ................ | A61B 1/0008 600/114 |
| 2005/0245960 A1 * | 11/2005 | Grundeman | ........... | A61B 17/02 606/192 |
| 2006/0173589 A1 * | 8/2006 | Gusler | ................ | B63G 8/08 701/21 |
| 2006/0259030 A1 * | 11/2006 | Utley | ................ | A61B 18/12 606/41 |
| 2008/0015408 A1 * | 1/2008 | Paolitto | ............ | A61B 17/00234 600/37 |
| 2008/0114288 A1 * | 5/2008 | Whayne | ........... | A61B 17/3421 604/27 |
| 2008/0114342 A1 * | 5/2008 | Whayne | ........... | A61B 17/0218 606/15 |
| 2008/0146881 A1 * | 6/2008 | Alimi | ................ | A61B 17/02 600/204 |
| 2008/0199065 A1 * | 8/2008 | Swain | ............... | A61B 1/00156 382/133 |
| 2008/0221591 A1 * | 9/2008 | Farritor | ............ | A61B 17/00234 606/130 |
| 2008/0262527 A1 * | 10/2008 | Eder | ................ | A61B 17/3403 606/185 |
| 2009/0048612 A1 * | 2/2009 | Farritor | ............... | A61B 19/2203 606/130 |
| 2009/0054909 A1 * | 2/2009 | Farritor | ............... | A61B 19/2203 606/130 |
| 2009/0062872 A1 * | 3/2009 | Chin | ............ | A61B 1/00082 606/86 R |
| 2009/0076536 A1 * | 3/2009 | Rentschler | ........ | A61B 17/0281 606/192 |
| 2009/0082634 A1 * | 3/2009 | Kathrani | ........... | A61B 17/0218 600/207 |
| 2009/0171373 A1 * | 7/2009 | Farritor | ............... | A61B 19/2203 606/130 |
| 2010/0036197 A1 * | 2/2010 | Mesallum | ......... | A61B 17/0218 600/104 |
| 2010/0168523 A1 * | 7/2010 | Ducharme | ......... | A61B 17/0218 600/207 |
| 2010/0217367 A1 * | 8/2010 | Belson | ................ | A61M 5/00 607/119 |
| 2011/0105850 A1 * | 5/2011 | Voegele | ............ | A61B 1/303 600/207 |
| 2013/0090666 A1 * | 4/2013 | Hess | ............... | A61B 17/0218 606/115 |

(56) References Cited

U.S. PATENT DOCUMENTS

| | | | |
|---|---|---|---|
| 2013/0178867 A1* | 7/2013 | Farritor | A61B 19/2203 |
| | | | 606/130 |
| 2013/0190775 A1* | 7/2013 | Piligian | A61B 17/0218 |
| | | | 606/130 |
| 2014/0277384 A1* | 9/2014 | Melsheimer | A61B 17/0218 |
| | | | 623/1.18 |
| 2015/0157192 A1* | 6/2015 | Piskun | A61B 1/00066 |
| | | | 600/114 |

* cited by examiner

Fig. 8A
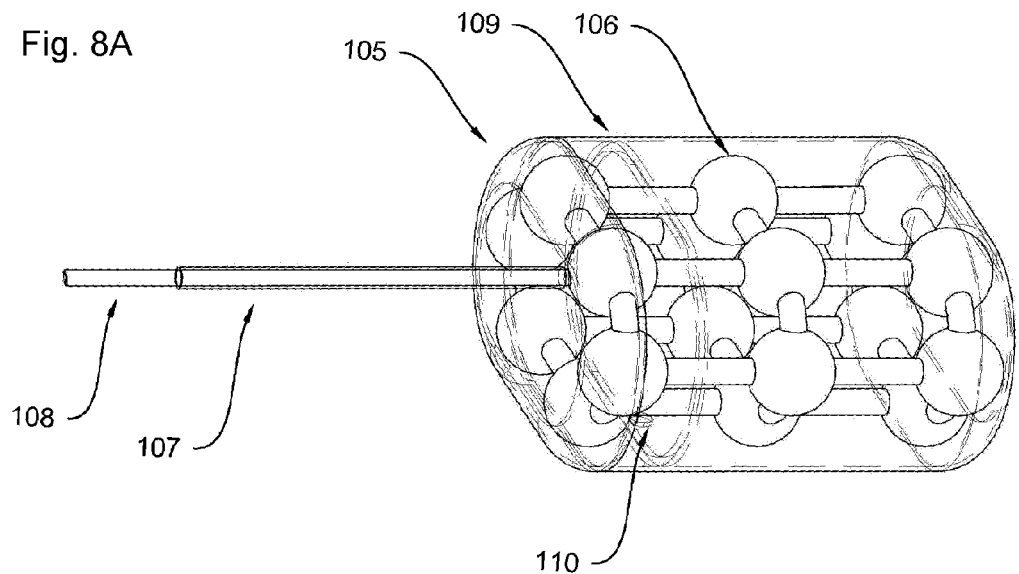
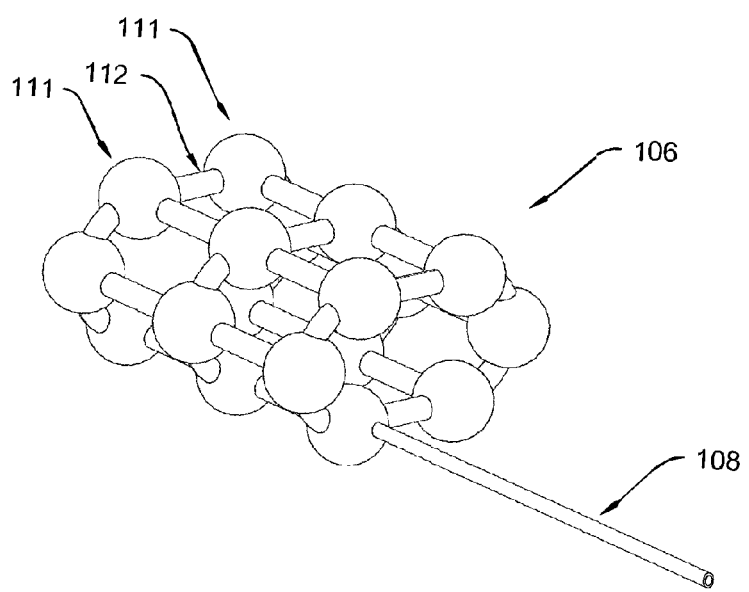
Fig. 8B

Fig. 8C
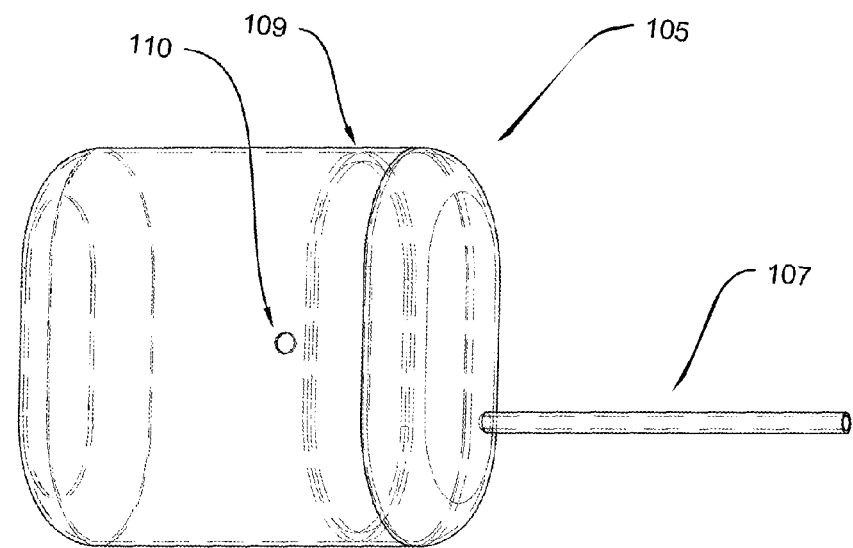
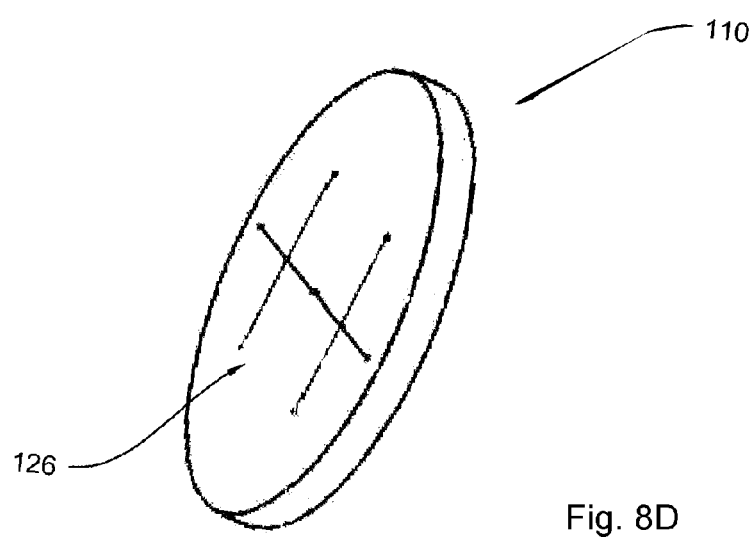
Fig. 8D

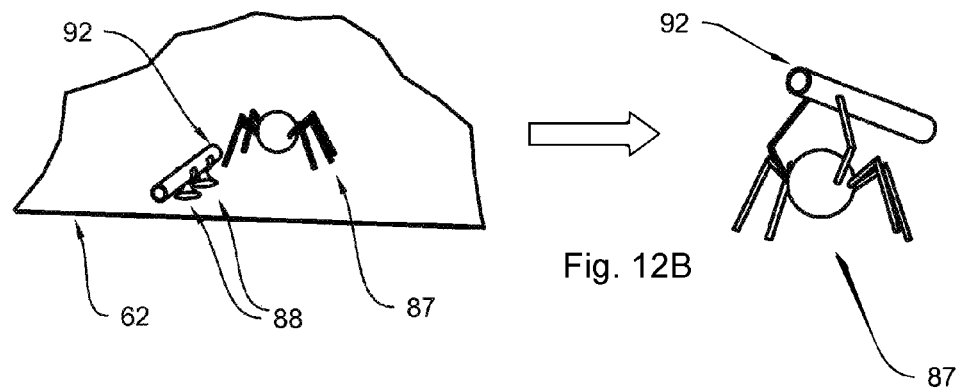
Fig. 12B
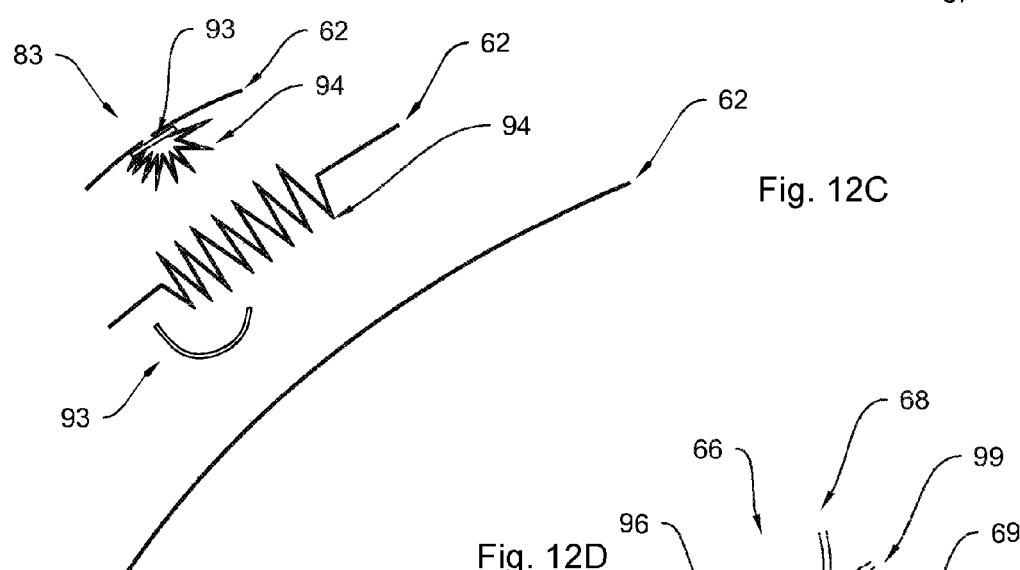
Fig. 12C
Fig. 12D
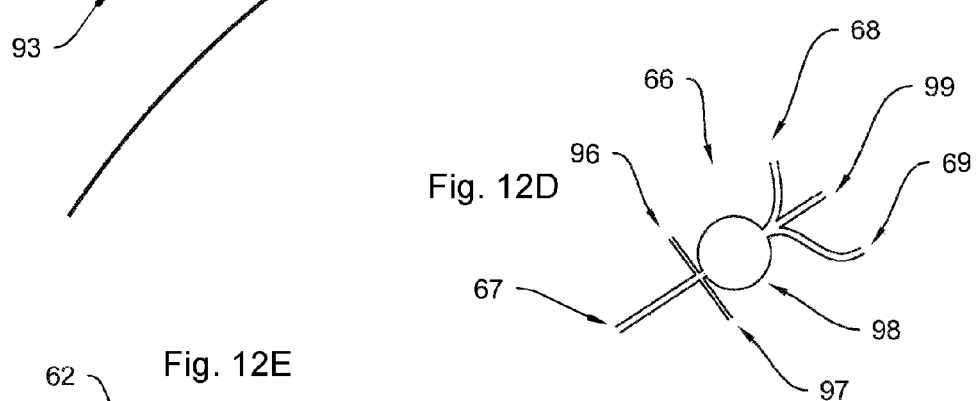
Fig. 12E
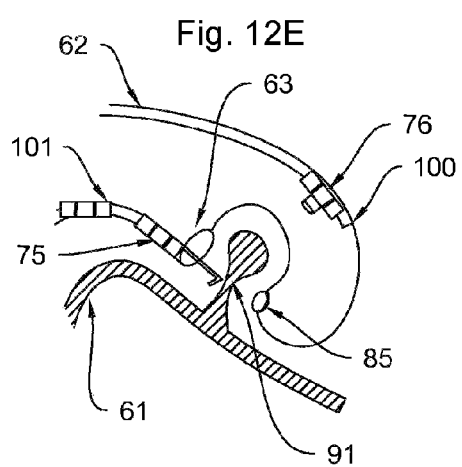
Fig. 12F
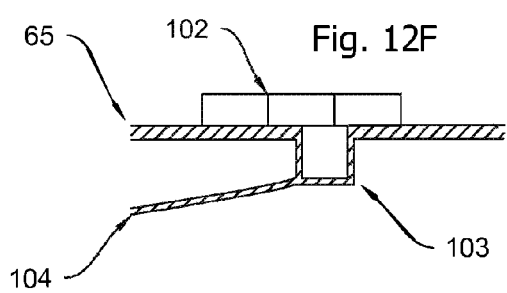

Fig. 13A
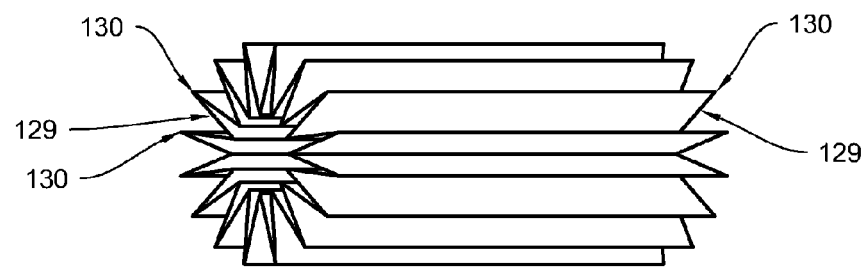
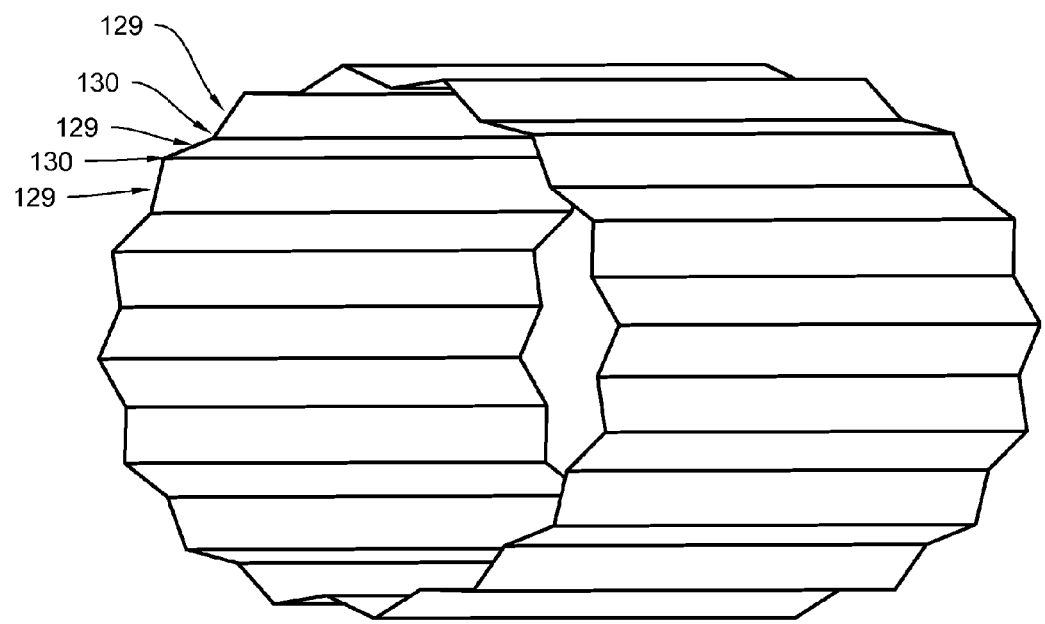
Fig. 13B

EXPANDABLE DEVICES, RAIL SYSTEMS, AND MOTORIZED DEVICES

CROSS-REFERENCE

This application is a continuation of U.S. application Ser. No. 13/877,660 filed on 3 Apr. 2013, which is a 371 national stage entry of PCT/US11/54829 filed on 4 Oct. 2011, which claims the benefit of U.S. provisional application Ser. No. 61/404,395 filed on 4 Oct. 2010, which are each incorporated by reference in their entirety.

TECHNICAL FIELD

The present invention relates to expandable devices, rail systems, and motorized devices.

BACKGROUND

Invasive surgical procedures are often used to address various medical conditions. When possible, minimally invasive procedures such as laparoscopy are preferred. However, known minimally invasive technologies such as laparoscopy are limited in scope and complexity due in part to 1) mobility restrictions resulting from using rigid tools inserted through incisions, 2) limited visual feedback and other drawbacks described in the medical literature [The pitfalls of laparoscopic surgery: challenges for robotics and telerobotic surgery. Ballantyne G H. Surg Laparosc Endosc Percutan Tech. 2002 February; 12(1):1-5].

Technical progress in the field has resulted in more flexible instruments that are less rigid and possess greater degrees of freedom for positioning the tiny tools located at the tip of the flexible scopes often shaped like snakes and having several internal conduits or ports through which lighting sources, irrigation or suctioning and other functional instrumentation can be threaded along the long axis of the scope. Nevertheless, there are still significant limitations in the use of these instruments as described in the literature [Karimyan et al. "Navigation systems and platforms in natural orifice translumenal endoscopic surgery (NOTES)". Int J Surg. 2009 August; 7(4):297-304. Epub 2009 May 27; Mintz et al. "Hybrid natural orifice translumenal surgery (NOTES) sleeve gastrectomy: a feasibility study using an animal model". Surg Endosc. 2008 August; 22(8):1798-802. Epub 2008 Apr. 25].

Continued advances in the field have imparted additional functionality to the flexible scoped instruments. However, among the still extant limitations, these instruments must be pushed through the body cavities by the operator without adequate visual or tactile feedback from the body organs and tissues, resulting in instances of puncturing through organ walls and other compilations. Hence, instruments have been devised that possess forward propulsion, the ability to advance forward without being pushed [e.g. Long, G: U.S. Pat. Nos. 7,226,410, 7,351,202; Hillel, J et al. U.S. Pat. No. 6,764,441; Grundfest at al. U.S. Pat. No. 5,337,732].

Another advance in the field is to employ several different devices, including micro robots, that function in cooperation with each other [Forgione et al., Surg Oncol. 2009 June; 18(2):121-9. Epub 2009 Jan. 14. "In vivo microrobots for natural orifice transluminal surgery. Current status and future perspectives; Michelini & Razzolini; Co-operative minimally invasive robotic surgery, Industrial Robot: Vol 35, No. 4, 2008, 347-3601. These robotic devices must still be propelled and guided by mechanical capabilities or by external means within the body cavities or lumens and must work alone or cooperatively within body spaces in which it is difficult to maneuver, and these robotic devices must be retrieved without undue burden on the patient or surgeon. Configured to perform specific tasks heretofore accomplished by manually delivered instruments, these robotic devices need appropriate space, protection from the internal body environments (designed to self-protect from foreign organisms or tissue), and energy means plus structural components to be able to maneuver inside the body—all this, is an unnecessary burden, since they are designed to perform a specific task(s) e.g., cutting, retracting, ablating, cauterizing, sewing, stapling, imaging and the like.

US 2009/0076536 (Rentschler et al.) describes a medical device positioning device comprising a rail supported by four legs in a swing-set-like structure. A medical device is moveably attached to the rail such that the device can move back and forth along the rail. Among other technical features, '536 does not teach an expandable sac comprising a rail, an expandable sac comprising a second inner sac in its lumen, an expandable sac comprising an diagnostic or therapeutic device in its lumen, or a malleable sac.

U.S. Pat. No. 6,605,037 (Moll et al.) describes an inflatable retraction device for retracting an organ inside a body to gain access to an adjacent tissue. The device comprises a first envelope enclosing a first inflatable chamber. Inside the first inflatable: chamber is the non-pressurized chamber, which is maintained in an expanded condition by the second inflatable chamber. Among other technical features, '037 does not teach an expandable sac comprising a rail, an expandable sac comprising an diagnostic or therapeutic device in its lumen, or a malleable sac.

There exists a need to fill significant gaps in the functionality of these various devices, taken alone or in unison. What is needed in the art are improved surgical devices for performing minimally invasive diagnostic or therapeutic procedures.

Among other advantages, the present invention, in one embodiment, is presented as an innovative expandable device capable of performing a vast number of diagnostic and therapeutic procedures.

SUMMARY OF THE INVENTION

The invention provides novel expandable devices, motorized devices, and rail systems for mobile devices.

A first aspect of the invention provides an expandable device for performing diagnostic and/or therapeutic procedures. An expandable device of the present invention comprises at least one expandable sac ('sac') and a tool housed therein, and is configured for operation while inside a body cavity. The sac is configured such that it can be manipulated from a collapsed state to an expanded state. An explamplary sac is an inflatable sac. An expandable device of the present invention further comprises one or more of following technical features:
   a. a rail system;
   b. a robotic tool in the lumen of a sac;
   c. a ported sac with a diagnostic or therapeutic (d/t) tool in the lumen of the sac;
   d. a multilayer configuration; and
   e. a malleable sac.

The invention contemplates an expandable device having any 1, 2, 3, 4, or all 5 of the above-listed technical features.

In one embodiment, the expandable device has a rail system comprising at least one rail in the lumen of the sac, and at least one railed device coupled to the rail for movement there on. Movement of the railed device(s) on the rail is provided by, for example, a motor such as an electromagnetic motor or an inch-worm type motor. Optionally, the expandable device comprises one or more robots and/or one or more d/t tools as railed devices. Optionally, the sac is tethered to the railed device such that the sac, or segment thereof, can be positioned by moving the railed device on the rail. Such expandable devices with a rail system are optionally provided with: a ported sac, a multilayered configuration, a malleable sac, or any combination thereof.

In one embodiment, the expandable device has a robotic tool ('robot') in the lumen of a sac. Optionally, the robot is a microrobot. Optionally the robot is a d/t tool. Optionally, the robot is a housekeeping robot. Optionally, the robot is a fragmented tool or a foldable tool. When the robotic tool is a d/t device, the expansion of the sac optionally provides a working environment for the d/t device. Optionally, the expandable device comprises a plurality of robots. Optionally, the expandable device comprises a rail system and at least one of the robots is a railed device and at least one of the robots is a non-railed device. Such expandable devices comprising a robotic tool are optionally provided with: a ported sac and at least one robotic d/t tool, a multilayered configuration, a malleable sac, or any combination thereof.

In one embodiment, the expandable device is a ported sac with a diagnostic or therapeutic (d/t) tool in the lumen of the sac. Such an expandable device comprises a sac with a port in a wall of the sac. The port can is sized, for example, to allow passage of the tool there through and/or access to a target site external to the sac. Optionally, the port is a valve. Optionally, the d/t tool is a robot. Optionally, the expandable device comprises a rail system and the d/t tool is a railed device. Such expandable devices comprising a ported sac are optionally provided with: a multilayered configuration, a malleable sac, or a combination thereof.

In one embodiment, the expandable device is a multilayer device. A multilayer device of the invention comprises an outer sac and at least one inner sac, wherein the at least one inner sac is in the lumen of the outer sac. Optionally, the inner sac is configured to be filled with a fluid to impart volume to the outer sac. Optionally, the device is configured to be filled with a fluid between the walls of the inner and outer sacs, for example, a lubricating fluid. Optionally, one or more of the inner and outer sacs comprises a tool (e.g. camera, lighting source, and/or robot), for example, in the lumen thereof. Optionally, the multilayer device comprises a first inner sac configured to be filled with a fluid to impart volume to the outer sac, and a second inner sac comprising a tool, for example, in the lumen thereof. Such multilayer devices are optionally provided with: a rail system, a malleable sac, or a combination thereof.

In one embodiment, the expandable device comprises a malleable sac. Optionally, the sac is configured for expansion by fluid pressure ('inflation'). For example, the sac is configured for inflation up being directly filled with a fluid (e.g. by access tube) or comprises an inner sac which is configured to be filled with a fluid (e.g. by access tube). Optionally, the wall of the malleable sac is made from any of: a polymer, a metal, or a dispersion of particles in a medium, a dynamic plastic, or a polymer malleable at a physiologically acceptable temperature. Optionally, the malleable sac is configured to remain expanded in the absence of luminal pressure. Optionally, the malleable sac is configured to contour against a surface (e.g. organ) upon expansion. Such expandable devices with a malleable sac are optionally provided with any of: a rail system, a robotic device, a ported sac, or any combination thereof.

Examplary expandable devices of the present invention are configured such that they can be inserted into a body cavity through a small passageway (e.g. incision or orifice) and expanded to provide a work environment for conducting a medical procedure in the body cavity.

A second aspect of the invention provides a mobile (motorized) device. The mobile device comprises an electromagnetic motor having three cars, wherein: a) each of the three cars comprises an electromagnet; b) each of the three electromagnets is independently operable; and c) the three electromagnets are arranged in a substantially collinear configuration such that a pole on each car is oriented for interaction with the pole of another car. In one embodiment, the three cars include a lead car, an intermediate car, and a trail car. The cars can be configured to move in an inchworm manner. Optionally, the mobile device is provided with the following configuration: the weight of the intermediate car is less than the lead car and less than the trail car; the weight of the lead car is less than the combined weight of the intermediate and trail car; and the weight of the trail car is less than the combined weight of the intermediate and lead car. Optionally, the mobile device further comprises a rail linking the cars for movement along a path. Optionally, the mobile device comprises a distance limiter for restraining the cars from moving further than a maximum distance from each other (e.g. the maximum distance of electromagnetic interaction between the cars).

Such a mobile device is optionally provided as a railed device in an expandable device of the invention. However, such a mobile device is alternatively used without expandable devices of the present invention where the mobile device can be coupled to any type of device for movement of the device (e.g. robot, microrobot, or imaging device).

A third aspect of the present invention provides a rail system. In one embodiment, the rail system comprises an inflatable rail for movement of a railed device. An inflatable rail of the invention comprises a conduit made from a flexible material, wherein: the conduit comprises an inlet for filling and inflating the conduit with a fluid; the conduit is configured to be turgid when inflated and flexible or flaccid when not inflated; and when turgid, the inflatable rail provides a support and a guide to the railed device for movement on the inflatable rail. Optionally, the rail comprises a fork in the conduit, wherein the fork branches a single conduit into a plurality of conduits, wherein each of the plurality of conduits can support a railed device when turgid. Optionally, the fork comprises a control circuit configured to differentially control the flow of fluid from the single conduit into the plurality of conduits. Optionally, the control circuit is a fluidic amplifier. Optionally, the railed device is a robot (e.g. microrobot) or comprises a d/t tool. Optionally, the railed device comprises an inchworm type motor or an electromagnetic motor.

Such an inflatable rail is optionally provided as a rail in an expandable device of the invention. However, such an inflatable rail is alternatively used without expandable devices of the present invention where the inflatable rail can be coupled with any type of railed device (e.g. robot, microrobot, or imaging device).

Any of the technical features listed above may be provided alone or in combination with any other to provide a device of the present invention. Accordingly, the invention also contemplates devices having any combination of the technical features listed above.

The invention also contemplates devices having any combination of the technical features listed above with any other embodiment taught herein (unless the combination of technical features is inconsistent with the express teachings of the embodiment).

BRIEF DESCRIPTION OF THE DRAWINGS

FIG. 8A depicts an expandable device of the invention. FIG. 8B through FIG. 8D depict parts thereof.

FIG. 12B through FIG. 12F depict parts thereof.

FIG. 13A and FIG. 13B depict a pleated expandable sac.

DETAILED DESCRIPTION OF THE INVENTION

Figure 1:
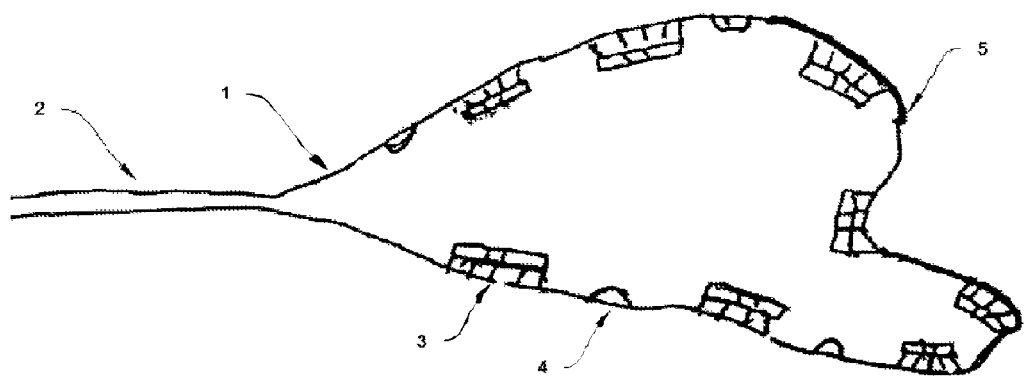
FIG. 1 depicts a device of the present invention comprising railed devices.

As used here, the following definitions and abbreviations apply.

"Examplary" (or "e.g." or "by example") means a non-limiting example.

"Expandable device" means a device comprising an expandable sac and at least one tool. In one embodiment, an expandable device is a multilayer device.

"Multilayer device" means en expandable sac comprising an outer expandable sac and an inner expandable sac in the lumen of the outer expandable sac.

"Substantially non-elastic" means the sac is substantially less elastic than a latex balloon. The elasticity of latex causes an inflated latex balloon to immediately contract to its original state after luminal pressure has been released. A malleable sac of the present invention is substantially non-elastic.

"Physiologically acceptable temperature" means a temperature at which an expandable sac may be expanded in a body cavity without causing substantial ablation of cells in the body cavity. Examplary devices of the present invention comprise an expandable sac that is malleable at a physiologically acceptable temperature. In one embodiment, the physiologically acceptable temperature is any of: less than about 50° C., less than about 45° C., less than about 40° C., or about 35 to about 37° C.

Expandable Sacs

In one embodiment, the invention provides an expandable device comprising at least one expandable sac and a tool.

The expandable sac can be any envelope defining a lumen and having at least two states: a collapsed state and an expanded state. In one embodiment, the sac is configured to be inserted into a body cavity in a collapsed state in which the sac has a minimal (or reduced) volume and/or cross sectional area, and then expanded in the body cavity to a state that has greater volume and/or cross-sectional area.

In one embodiment, the expandable sac is any of: a malleable envelope, a flexible envelope (e.g. membrane or balloon), or a pleated envelope.

In one embodiment, the expandable sac is made from a material that is any of: flexible and substantially non-elastic, elastic, viscoelastic, viscoplastic, compliant, flexible and non-compliant, malleable, or non-malleable. The skilled artisan will recognize that such sacs are not limited to any particular material. There are many known materials that can be configured with one or more of such physical properties.

The expandable sac can be made from any material, for example, a metal, a polymer, or a dispersion of particles in a medium. Examplary metals include malleable metals such as gold, platinum, palladium, and silver. Examplary polymers include semi-crystalline and amorphous polymers. Examplary polymers include any of the following types: polyolefins (e.g. Low density polyethylene (LDPE), high density polyethylene (HDPE), or polypropylene (PP)), styrenics, vinyls (e.g. PVC), acrylics (e.g. polymethyl methacrylate), fluoropolymers (e.g. PTFE, CTFE), polyesters (e.g. PET), polyamides (Nylons), polyimides, polyethers, and sulfur containing polymers.

In one embodiment, the expandable sac comprises pleats. Such a pleated envelope comprises segments (sac wall portions) connected by flexible pleats or preformed fold lines. The segments are optionally rigid or flexible. If the segments are flexible, the pleats can have greater flexibility than the flexible segments.

In one embodiment, the expandable sac is a dip molded or blow molded envelope. Examples of such are well known in the art. A blow molded envelope can be provided, for example, by a) beginning with a plastic resin hot tube (a parison) or pre-form; b) the parison is placed within a split mold with a hollow cavity; c) the mold sides are then clamped together, pinching and sealing the parison tube; d) air is blown into the tube, which expands the hot resin wall into the shape of the cavity; e) the mold is cooled with water solidifying the resin into the desired shape.

In one embodiment, the expandable sac is sized to fit in a body cavity or body lumen ('body cavity') of a patient (e.g. human) while expanded. Examples of patients include a human, a ruminant, a canine, and an elephant. Examples of body cavities in which the sac can be configured for placement include the abdomen, colon, large intestine, small intestine, GI tract, vagina, uterus, fallopian tubes, thoracic cavity, pleural cavity, sinuses, urethra, ureters (e.g. a cavity of a human). The sac can also be sized for small lumens or vessels filled with a fluid (e.g. blood or lymphatic vessels).

In one embodiment, the expandable sac comprises at least one tool in its lumen. Optionally, the sac is configured such that expansion of the sac provides one or more of: a work environment for the tool at a target site, retraction of organs or other tissue from the target site, and stabilization of the sac against the walls of a body cavity.

In one embodiment, the sac is configured to support a rail and a railed device. In such a device, the sac is configured such that, at least upon expansion, a work environment is provided that railed devices can move within.

In one embodiment, the sac comprises at least one port.

In one embodiment, the sac comprises an access tube.

In one embodiment, the sac comprises a port and an access tube.

In one embodiment, the device is a multilayer device comprising an outer sac and at least one inner sac in the lumen of the outer sac. Optionally, one or more of the outer and inner sacs comprises an access tube. Optionally, one or more of the outer and inner sacs comprises a port.

In one embodiment, the sac is transparent. Such a sac is especially useful for allowing imaging of a body lumen by a camera mounted in the lumen of the sac. Examples of materials useful for creating transparent sacs include PVC and nylon. Other transparent materials that can be configures as expandable sacs are well known in the art.

In one embodiment, the sac comprises sensors (e.g. motion sensors), for example, embedded in the sac wall.

In one embodiment, the sac is an outer sac comprising traction-imparting protrusions or filaments extending from the exterior of the sac.

In one embodiment, an expandable sac is configured for expansion by inflation or other means for providing luminal pressure.

In one embodiment, the sac is made from a material that is expandable, durable, and of biocompatible material. Examples of such materials are well known in the art.

Malleable Sacs

In one embodiment, the sac is malleable and/or ductile ('malleable sac'). Malleability is a material's ability to deform under compressive stress. Ductility is a material's ability to deform under tensile stress. Useful malleable sacs according to the present invention are those which are deformable and substantially non-elastic. In one embodiment, a malleable sac is both malleable and ductile. Any portion (surface area) of the envelope can be malleable, for example, the entire envelope, a majority of the envelope, or segments of the envelope.

The malleable sac can be made from any malleable material. In one embodiment, the malleable sac is made from a material selected from: a thermoplastic resin, a viscoplastic, a viscoelastic, or a dilatant. Useful materials for producing a malleable sac are not limited to any particular structure. A wide variety of materials can be configured into a malleable sac. In one embodiment, the malleable sac is made from a material selected from: a metal, a polymer, a wax, a gum, a clay, or a plant hydrogel.

In one embodiment, the malleable sac is made from a thermoplastic resin. Thermoplastic resins are polymers which become a liquid when heated to their melting point (Tm) and freeze when cooled below their glass transition temperature (Tg). Many useful thermoplastics are known in the art. Many thermoplastics become malleable at a temperature between their Tg and Tm. In one embodiment, the malleable sac is made from a thermoplastic that is malleable at a physiologically acceptable temperature. Alternatively, the malleable sac can be made from a thermoplastic that is malleable at a temperature above that which is physiologically acceptable. In such an embodiment, the expandable device can comprise heating elements to impart malleability to the sac when desired. If the device is intended for use in a live patient, the patient can be protected from the high temperatures using a layer of insulation wrapped around the expandable sac that can be removed when sac malleability is no longer desired.

In one embodiment, the malleable sac is made from a viscoplastic. A viscoplastic is a material that exhibits inelastic plastic deformation, i.e. the material undergoes unrecoverable deformations when a load level is reached. Although viscoplastics are not limited to any particular material, a viscoplastic can typically be identified as a material in which deformation depends on the rate at which loads are applied. A number of viscoplatics are known in the art. For example, many thermoplastic resins can be configured as viscoplastics.

In one embodiment, the malleable sac is made from a viscoelastic. A viscoelastic is a material that exhibits both viscous and elastic characteristics when undergoing deformation. Although viscoelastics are not limited to any particular material, a viscoelastic can typically be identified as a material having one or more of the following properties: a) if the stress is held constant, the strain increases with time (creep); b) if the strain is held constant, the stress decreases with time (relaxation); c) the effective stiffness depends on the rate of application of the load; d) if cyclic loading is applied, hysteresis (a phase lag) occurs, leading to a dissipation of mechanical energy. A number of viscoelastics are known in the art. For example, many thermoplastic resins can be configured as viscoelastics.

In one embodiment, the malleable sac is made from a dilatant. A dilatant is a material in which viscosity increases with the rate of shear strain. A number of dilatants are known in the art. For example, a dilatant can comprise a cross-linked polysiloxane (e.g. polysiloxane-boron) polymer, for example, as seen in Silly Putty™, a dilatant containing 65% dimethyl siloxane (hydroxy-terminated polymers with boric acid), 17% silica (crystalline quartz), 9% thixotropic (castor oil derivative), 4% polydimethylsiloxane, 1% decamethyl cyclopentasiloxane, and 1% glycerine.

In one embodiment, the malleable sac is made from a polymer. In one embodiment, the polymer is a semi-crystalline polymer or an amorphous polymer. In one embodiment, the polymer is a polysiloxane, a shape memory polymer, a dynamic polymer, a viscous polymer, a viscoplastic polymer, a viscoelastic polymer, or a thermoplastic resin. Polymers are especially useful materials for making malleable sacs because they have readily tunable properties. The skilled artisan will recognize that the properties of a polymer (e.g. malleability, viscosity, viscoelasticity, viscoplasticity, Tg, Tm, etc) can be tuned by configuring the polymer in a number of manners, for example, by using appropriate branching, cross-linkages, by incorporation into copolymers (e.g. block or graft) or mixed polymers, or by mixing with appropriate excipients (e.g. plasticizer).

In one embodiment, the polymer is a thermoplastic resin configured in a manner to impart malleability and/or ductility. Examples of thermoplastic polymer types that can be configured to provide a malleable sac material include acrylates (e.g. a polymethyl methacrylate), fluoropolymers (e.g. a PTFE, a CTFE, or a PVDF), polyesters (e.g. a PET (polyethylene tetrephthalate), a PTFE (polytetrafluoroethylene), or other types of polyethylene), polyolefins (e.g. a LDPE or a PP), a polycarbonate, a thermoplastic elastomer (e.g. thermoplastic polyurethane), or a low molecular weight thermoplastic resin or a blend of a thermoplastic resin and a particulate material, for example, as described in U.S. Pat. No. 7,157,140).

In one embodiment, the malleable sac or segments thereof is made from a shape memory plastic or a macroscopically responsive structurally dynamic polymer. A shape memory plastic can be configured to take on a different shape following activation (e.g. by physical, chemical, or electromagnetic radiation (e.g. light) based activation). Examples of such are known in the art, for example, as described by Thompson ("Intelligent plastics change shape with light", MIT Tech Talk; Volume 49—Number 25). In one embodiment, the macroscopically responsive structurally dynamic material is a thermoresponsive material, a hemoresponsive material, a mechanoresponsive material, a photoresponsive materials, or an electroresponsive materials, for example, as described by Woojteck et al. (Using the dynamic bond to access macroscopically responsive structurally dynamic polymers; Nature Materials. Vol 10, January 2011).

In one embodiment, the malleable sac is made from a clay, e.g. a dispersion of particles in a medium such as a plasticizer. Optionally, the clay is a polymer clay (e.g. PVC dispersed in a plasticizer) or silica clay (silicon particles dispersed in a plasticizer).

In one embodiment, the malleable sac is made from a metal. Examplary malleable metals include malleable metals such as gold, platinum, palladium, and silver. A malleable sac can be provided, for example, by configured a thin envelope made of a malleable metal. In one embodiment, the malleable sac is an envelope having a malleable metal wire frame and a transparent polymer membrane laid across the wire frame.

In one embodiment, the malleable sac is made from a wax. Useful waxes include carboxylic acid waxes, fatty alcohol waxes, paraffins, montan waxes, mineral oil waxes, gel waxes, microcrystalline waxes, gels, and cracked polyethylenes, In one embodiment, the malleable sac is made from a gum, a mucopolysaccharide (e.g. Viscoat, a viscoelastic solution) or a proteoglycan (e.g. as described in European Patent Application EP0466966).

In one embodiment, the malleable sac is made from a plant hydrogel. Examples of useful plant hydrogels are described, for example, in "Hydrogels, Latexes and Resins" [http://botany.csdl.tamu.edu/FLORA/328Fa1198/resins.html].

In one embodiment, the malleable sac is made from a coated elastomer, e.g. as detailed in Mandavi et al. (PNAS Feb. 19, 2008 vol. 105 no. 7 2307-2312). Such an elastomer can be configured in a manner to impart malleability.

In one embodiment, the malleable sac is made from a combination of different malleable materials. Optionally, the different malleable materials are arranged in a segmental or quilt-like manner to impart differential malleable characteristics to different segments of a sac wall.

In one embodiment, the malleable sac comprises a plurality of sac wall portions ('segments') with different malleability or deformability (resistance to deformation), for example, to provide differential expandability of the plurality of segments. Such a sac can be obtained, for example, by providing the portions with different malleable materials or by configuring the portions with different thicknesses of the same material.

In one embodiment, the malleable sac is a pleated sac comprising malleable pleats (malleable fold lines).

In one embodiment, the wall of the malleable sac (or segment thereof) is provided with a thickness such that, increased by stressing the wall (by compressive or tensile stress), the wall surface area can be by at least any of: 2 fold, 3 fold, 4 fold, 6 fold, or 10 fold without breaking. Optionally, the elasticity of the material is such that the wall surface area remains increased by at least about 20% or 50% for one minute after the stress is removed. The skilled artisan will appreciate that the maximum deformability (e.g. extent that a malleable sac wall can be stretched before breaking) can be dependent on the properties of the malleable material itself and the thickness of the wall.

In one embodiment, the malleable sac is configured to be expanded from a collapsed state by imparting pressure on the luminal wall (e.g. filling the sac with a fluid) and then remain expanded in the absence of said pressure on the luminal wall (i.e. they are self-supporting). Optionally, the malleable sac is configured to retract an organ upon expansion and does not collapse the stress of the organ in the absence of luminal pressure.

In one embodiment, an expandable sac is configured with a malleability such that it can be deformed by smooth muscles but retains its shape and/or structural integrity in the absence of luminal pressure or external pressure (i.e. the sac is self-supporting).

In one embodiment, an expandable sac is configured with a malleability such that it can be deformed against a body cavity wall without substantially harming the patient, but retains its shape in the absence of luminal pressure (i.e. the sac is self supporting).

In one embodiment, the lumen of the sac comprises (or is configured to be filled with) a fluid (e.g. viscous fluid), for example, to impart volume to the sac by fluid pressure.

Although a collapsed malleable sac (e.g. folded or rolled) can be configured to expand (unfold or unroll) to a predetermined shape (e.g. upon imparting a target expansion pressure), a superior property of examplary malleable sacs is that the sac can be deformed beyond and/or irrespective of a preconfigured shape (e.g. shape determined when forming a sac by molding). For example, after expansion to a predetermined shape by inflation at a first pressure, a portion of the wall ('segment') can be locally deformed (e.g. stretched) into a desired fold or other small cavity (e.g. diverticulum) in the wall of a larger body cavity.

In one embodiment, the malleable sac is transparent. A transparent sac can be made from transparent malleable polymer (e.g. a polycarbonate film).

In one embodiment, the device comprises a malleable sac comprising a port. Optionally, the malleable sac is an outer sac and the device further comprises an inner sac in the lumen of the outer sac. Optionally, at least one of the inner or outer sacs comprises an access tube. Optionally, both the inner and outer sacs comprise ports. Optionally, one or more of the sacs is transparent.

With the teachings provided herein, the skilled artisan can now select materials appropriate for producing a malleable sac. The skilled artisan will recognize that the malleability and/or deformability of the sac is dependent on factors such as the physical properties of the material, the thickness of the material, and the environment of the material (e.g. temperature, physical, chemical, or electromagnetic energy forces applied to the material).

Multilayer Devices

In one embodiment, the expandable device is a multilayer device. According to the present invention, a multilayered device comprises an outer sac and at least one inner sac in the lumen of the outer sac.

In one embodiment the inner sac is configured for expansion by being filled with a fluid to impart volume and shape to the outer sac (e.g. fluid pressure).

In one embodiment, the inner sac is configured for housing a tool (e.g. robot) in its lumen, for example, to compartmentalize the tool. Optionally, the expandable device comprise a plurality of inner sacs, each housing a different tool.

In one embodiment, the expandable device comprises a plurality of inner sacs. Optionally, one or more inner sacs house a tool (e.g. robot) and one or more inner sacs are configured for expansion, e.g. to provide a framework to the expandable device. Optionally, the plurality of inner sacs comprises different fluids (e.g. gel/gas, gas/liquid, liquid/gel).

In one embodiment, the expandable device comprises a first inner sac in the lumen of an outer sac, and a second inner sac in the lumen of the first inner sac. Optionally, the space between the walls of the first and second inner sacs is filled with a fluid, for example to cushion the contents (e.g. robot) of the second inner sac.

In one embodiment, the expandable device comprises an outer sac, a first inner framework sac in the lumen of the outer sac, a second inner sac in the lumen of the outer sac, and a third inner sac in the lumen of the second inner sac. The second and/or third inner sacs optionally house a tool in the lumen.

In one embodiment, the outer and/or inner sacs comprise ports. Optionally, an outer sac and an inner sac comprise ports that are configured to be aligned, for example, as detailed in Example 4. In one embodiment, a port is provided on any sac that houses a tool (e.g. robot).

In one embodiment, the inner sac is attached or embedded to the outer sac. Optionally, the inner sac provides a framework. Optionally, the framework is an inflatable conduit embedded in an outer sac. Such a conduit can be used, for example, to expand the outer sac and/or provide rigidity in the outer sac. Optionally, the inflatable conduit is provided segmentally or localized about the outer sac, for example to provide expansion and/or rigidity in some segments of the outer sac wall but allow other segments to remain flexible. The conduit can also be configured as a rail (inflatable rail) that serves as both a framework for the device and a rail for guiding railed devices.

In one embodiment, a multilayer device comprises sacs provided in any of the following arrangements: arranged as
 a. Successive;
 b. Contiguous;
 c. Budding out from each other (evaginating);
 d. Budding in (invaginating);
 e. Involuting (shaped in whorls that obscure their axis of location);

Expansion

An expandable sac of the present invention is configured for expansion from a collapsed state. The present invention contemplates devices configured in any manner that allows expansion by any mechanism.

In one embodiment, the envelope (wall) of an expandable sac can configured for expansion by providing the sac as any of: a flexible envelope (e.g. membrane), a malleable envelope, a pleated envelope, or a combination thereof.

In one embodiment, a sac is configured for expansion by fluid pressure, i.e. by filling the sac with a fluid (e.g. inflation). Optionally, a sac configured for expansion by fluid pressure is fluidly connected to an access tube. In another embodiment, the sac is configured for expansion by an expandable framework (e.g. "T" framework for placement between two organs).

Useful fluids that can be used to expand a sac include gasses, liquids, gels, viscous liquids, and particulates or semi-solids that can be pumped or otherwise filled into a sac to cause expansion of the sac. In one embodiment, the device comprises one or more access tubes fluidly connected to one or more sacs of the device such that a fluid can be pumped in (or out) of the one or more sacs, thereby expanding the sac(s). Optionally, the access tube is flexible (optionally malleable) to allow curves in the tube. In such an embodiment, the access tube can be connected to a fluid pump provided outside of the patient (or other work environment). As an alternative to an access tube, an expandable sac can contain a pressurized vessel, filled with the fluid, comprising a fluid release valve that allows release of the pressurized fluid into the lumen of the expandable sac, thereby expanding the sac.

Useful expandable mechanical frameworks include a framework of one or more inner sacs that are expandable (e.g. by fluid pressure), e.g. as detailed in or an expandable scaffolding, for example, a magnetically detailed in US 2009/0287293 (Mailhot).

In one embodiment, the expandable sac is configured to fold along one or more segments, for example, by providing pleats that are flexible or malleable.

In one embodiment, an expandable sac is configured for expansion by pleating and/or packing (e.g. telescopically) segments of the sac wall in any known manner of pleating or packing such that expansile pressure exerted by any mechanism can unfold or lengthen the sac wall.

In one embodiment, the sac is configured expansion upon the lumen reaching a target expansion pressure. Optionally, the target expansion pressure is less than about any of: 100 psi, 75 psi, 50 psi, 25 psi, 10 psi, 5 psi, 2 psi, or 1 psi. Optionally, the target expansion pressure is greater than about any of: 1 psi, 2 psi, 5 psi, 10 psi, 20 psi, 30 psi, 50 psi, or 75 psi. Such a sac is not limited to a sac made from any particular material. The skilled artisan will recognize that a sac's target expansion pressure is dependent on the properties of the sac material, the thickness of the sac wall, and the environment of the sac (e.g. temperature). Optionally, the sac has a plurality of target expansion pressures. For example, the sac can be configured a folded sac with a plurality of pleats, some of which unfold at a first target pressure, and some of which unfold at a second target pressure. As another example of a sac with a plurality of target expansion pressures, a malleable sac can be collapsed (e.g. folded or rolled) and configured to expand (unfold or unroll) at a first target pressure and then deform (e.g. by stretching) at a second target pressure. Such a sac with a plurality of target expansion pressures is useful, for example, to induce one expanded shape at the first target pressure, and then a second expanded shape (predetermined or not) at the second target pressure. Optionally, the second target pressure is provided by means other than inflation, for example, a sac shaping tool such as a robot that presses against the luminal wall. Malleable sacs are especially useful for providing such a configuration.

An expanded sac can be collapsed by any means, for example, to retract the device out of a body cavity through a small incision or other passageway. For example, the sac can be configured to collapse by evacuation or clearing of a fluid filled therein. Additionally or alternatively, an expanded sac can be collapsed using forceps or other means to squeeze the sac into a collapsed state. Additionally or alternatively, a malleable sac can be optionally configured to be collapsed by cold-shrinking the sac.

In one embodiment, the lumen of the sac comprises (or is configured to be filled with) a viscous fluid, for example, to impart volume to the sac.

In one embodiment, one or more robots (e.g. microrobots) are provided for moving and/or coupling access tubes, inner sacs, or frameworks as needed. For example, robotic devices moving as railed or non-railed devices can open or close access tube connections in conduits to fill or empty the conduits, Alternately, robotic devices insert a tubular conduit (or segment thereof)—a free-standing conduit (as opposed to network of embedded conduits in wall of the sac) into the embedded conduit portals in order to remove and divert the fluid into an adjacent sac or else into a main transport tube (in order to remove the fluid out of the expandable device entirely).

Additional means to expand a sac(s) and simultaneously to shape sac(s) as desired include: deploying an expandable framework or a solid, lattice framework into a preconfigured shape and then adding or subtracting from the framework or else modifying the shape of the framework using robotic devices. This can occur, as an example, by introducing a heating tool on the robotic device to a modular segment of a framework, thereby shrinking its size thus imparting a desired shape need for the optimal performance of the procedure on the target organ or tissue.

In one embodiment, a substantially viscous material flows in the sac lumen imparting shape to the sac.

In one embodiment, the a fluids expansion and/or lubrication between the walls of an inner and outer sac.

In one embodiment, fluid supplied to the inner wall of the sac changes its elasticity (e.g. in a material having environment-dependent properties) imparting additional expandability in targeted segments of the wall of the sac.

In one embodiment, the expandable sac is filled with micro-crystalline collagen, for example, for incorporation in any sac wall for segmented or localized thickening of wall sacs. Examples of such micro-crystalline collagen are described in U.S. Pat. No. 3,443,261.

In one embodiment, the expandable sac is filled with a chitosan, for example, which can be configured to interchange between a liquid and solid like state. This is useful, for example, as a sac wall composition and for shaping an expandable sac in either in a diffuse or segmental manner. As example of such chitosan is described by Chenite et al. (Biomaterials. 2000 November; 21(21):2155-61. Novel injectable neutral solutions of chitosan form biodegradable gels in situ).

In one embodiment, gas or liquid contents can be removed by tubular attachments or else rendered into another more convenient form such as a powder (e.g. by mixing with a powder or by freezing) without being allowed to react with the body linings.

Ports

In one embodiment, the device comprises one or more ports in a sac wall. A port according to the present invention is a passageway in a sac wall connecting the lumen of the sac with the periphery of the sac. Optionally, a port of the device is sized to allow passage of a tool there through, for example, a d/t device.

In one embodiment, the port is a valve. A valve is a port configured to have two states: opened and closed. The port can be any type of known in the art. For example, the port can be a two way valve such as a butterfly valve, a ball valve, a slide valve, or a self-sealing valve. Optionally, the valve is configured to provide a fluid-tight seal when closed and allow passage of a tool through it when open. Optionally, the device comprises a valve actuator for opening and/or closing the valve.

In one embodiment, the expandable device is a multilayer device comprising an inner and outer sac, wherein both sacs have a port. Optionally, the ports are configured to align to allow the passage of a tool from the lumen of the inner sac to the periphery of the outer sac.

In one embodiment, ports comprise an adhesive, for example, to provide a fluid-tight seal.

A port allows access to the periphery of the sac wall (e.g. by robot passing there through).

Railed Devices

In one embodiment, the expandable device has a rail system comprising a rail and a railed device coupled to the rail for movement there on. Useful railed devices comprise a rail coupler for coupling the railed device to the rail for movement there on. Optionally, the coupler is configured for supporting, stabilizing and/or securing the railed device on the rail. Optionally, the railed device comprises a motor for moving the railed device along the rail.

In one embodiment, the railed device carries a tool. The tool can be any tool (e.g. as taught herein). For example, the tool can be a robot, a microrobot, a d/t instrument, or a housekeeping tool. Such a railed device can be used, for example, to transport and position the tool.

In one embodiment, the railed device is tethered to a sac wall. Optionally, a plurality of railed devices are tethered to a sac wall. Examples of such are detailed in Example 5 and Example 13. Such a railed device can be used, for example, to move or position a sac wall, for example, to move the entire expandable device, a portion of the sac wall, or to impart bends or articulations in the sac wall. Optionally, the railed device is tethered to the sac wall by retractable pylon (i.e. an attachable/detachable tether). Such a railed device can be used to selectively or transiently tether a desired segment of the sac wall for movement thereof. A retractable pylon can interface the sac wall, for example, using clips, magnets, key/keyhole combinations and the like.

The rail coupler can be any coupler that couples the railed device to the rail for movement thereon and optionally supports, stabilizes, and/or secures the railed device on (or in) the rail. In one embodiment, the rail coupler comprises any of: a wheel, a protrusion, a cavity, a sled, a walking member, a gear, a pulley, a hook, or a magnet. A wheel can be used, for example, to roll a railed device on a rail. A protrusion can be used, for example, sit a railed device in a groove of a rail (e.g. in grooved rails or grooved fluidic rails). A cavity (e.g. groove) can be used, for example, to sit and/or stabilize a railed device on a protrusion of a rail. A sled can be used, for example, to slide a railed device about a rail. A walking member (e.g. appendages as known for walking robots) can be used, for example, to transiently contact a rail as a railed device walks about the rail. A gear can be used, for example, to interface with a rack as in a rack and pinion configuration. A magnet can be used, for example, to stabilize a railed device to the rail or levitate a railed device on a rail. A hook can be used, for example, to secure a railed device to a rail. A pulley can be used, for example, to couple the railed device as a conveyor belt-type device. Optionally, the rail coupler is configured for coupling in a railed microfluidics rail system, for example, as described by Chung et al. ("Guided and fluidic self-assembly of microstructures using railed microfluidic channels"; Nature Materials 7, 581-587 (2008)). Couplers that provide stabilization or securing of the railed device optionally keep the railed device in contact with the rail, for example, to avoid derailing of the railed device. Such a coupler can be used to keep the railed device in the proper orientation and/or to provide vertical and/or lateral support, e.g. to avoid the railed device from tipping over or falling off the rail. Examples of useful components for such stabilization or securing include hooks, magnets, cavities, protrusions, as described above.

Motors

In one embodiment, a railed device comprises a motor for moving the railed device along the rail. The motor can be any motor that imparts such movement along the rail.

Useful motors include linear actuators, inchworm motors, electromagnetic motors, and the like.

In one embodiment, the motor is a linear actuator. Examples of linear actuators of any of the following types: rotary stepper motors, rotary servo motors, voice coil, screw, piezoelectric device, solenoid, or pneumatic pump actuators. Examples of such linear actuators are well known in the art.

In one embodiment, the motor is an inchworm motor. An inchworm motor is a motor comprising at least two railcars, a lead car and a trail car, wherein each rail car moves independently to provide an inchworm-like movement. An inchworm motor operates by extending the lead railcar (e.g. moving along the track) and then stopping or slowing the first railcar, and then moving the second (or additional) railcar to meet the first rail car. Optionally, the inchworm motor is an electromagnetic inchworm motor, wherein the movement of one or more rail cars is imparted by attractive/repulsive magnetic forces. Optionally, the inchworm motor is an attach-extend type motor, wherein one car is transiently mechanically fixed to the rail (by breaking means such as a friction pad or clamp) and another car is pulled to or pushed from the fixed car.

In one embodiment, the inchworm motor is an electromagnetic motor. Any inchworm type electromagnetic motor is useful according to the present invention.

In one embodiment, the motor is an inchworm type electromagnetic motor comprising three railcars, a lead car, and intermediate car, and a trail car, each comprising an electromagnet, for example, as detailed in Example 1 and Example 2. Optionally, the railed device comprises a distance limiter for restraining the cars from moving a maximum distance from each other (e.g. a cable or membrane). In such a motor, the electromagnets are configured to attract and repel the electromagnet(s) on adjacent cars, thereby moving at least one car. Although an electromagnetic inchworm motor can be configured as an attach-extend type motor, the inventor has surprising discovered that the motor can be configured without a means of fixing (breaking) the railcars to the rail. In such a three-car electromagnetic motor, the rail cars can be configured with the following specifications: the intermediate car weighs less than the lead and trail car, the lead car weighs less than the intermediate car and the trail car combined, and the trail car weighs less than the lead and intermediate car combined, e.g. as discussed in Example 2.

This configuration surprisingly provides for inchworm-type movement without requiring any car to be transiently fixed to the rail because one or more heavier rail cars (i.e. cars with greater inertia considering mass and friction) remain relatively stationary while a lighter car (i.e. cars with less inertia considering mass and friction) moves by electromagnetic forces (repulsion or attraction) imparted by interaction of the electromagnets. Such an electromagnetic motor is also useful alone, for example, without an expandable device of the present invention and/or without a rail.

In one embodiment, the inchworm motor is an attach-extend type motor, wherein one car is transiently mechanically fixed to the rail and the other car is moved relative to the fixed car (e.g. by attraction or repulsion). An attach-extend type motor comprises at least two cars, wherein a first rail car comprises mechanical fixing means (e.g. clamp or break) and the motor comprises means for movement of the second rail car relative to the first rail car, for example, by attraction or repulsion (e.g. spring, magnet, electromagnet, linear actuator). The fixing means can be a clamp such as a piezoelectric clamp or a friction-inducing means such as an electromagnet. Examples of useful attach-extend type inchworm motors and other motors are described in U.S. Pat. No. 6,040,643, US 2009/0115284, U.S. Pat. No. 6,380,661, and Tucker ("Actuation for Mobile Micro-Robotics"; Obtained from the URL: http://www.ece.ncsu.edu/erl/microrobotics/actuation/actuation.html on 28.09.2011).

Another useful inchworm motor is described by Fuchiwaki et al.: ("Development of 3-DOF Inchworm Mechanism for Flexible, Compact, Low-Inertia, and Omnidirectional Precise Positioning: Dynamical Analysis and Improvement of the Maximum Velocity Within No Slip of Electromagnets"; Mechatronics, IEEE/ASME Transactions on; Volume: PP Issue: 99, page(s): 1-12).

Other useful motors include any motors known in the art for moving robots or microrobots or used for movement in micro-electromechanical systems (MEMS).

Although the motors described herein can be used to move a railed device about a rail, the invention also contemplates expandable devices comprising non-railed robots comprising any of said motors as a means for movement.

Rails

According to the present invention, an expandable device optionally comprises a rail such that a railed device can move along the rail. The rail can be coupled to the sac by providing the rail in the lumen of the sac and/or providing one or more attachment points between the sac and the rail. The rail can be any member configured to support to a railed device and provide a track along which the railed device can move.

In one embodiment, the rail is any of: flexible or rigid, fragmented or continuous, embedded in the sac wall, mounted to the sac wall, contiguous or discontiguous with the sac wall.

In one embodiment, the rail provides a member configured to provide lateral support to a railed device. Optionally, the member is a protrusion or a groove.

In one embodiment, the rail is permanently or reversibly fixed to the sac.

In one embodiment, the device comprises a plurality of rails. Optionally, the plurality of rails is in the same sac. Optionally, the each of the plurality are in different sacs.

In one embodiment, the rail is a flexible rail. Such a rail is useful, for example, to allow the rail to change shape in order to bend around corners and/or fit through small passageways as the expandable sac is maneuvered in or through a body cavity.

In one embodiment, the rail is a fragmented and/or modular rail configured for assembly and disassembly within the expandable sac. Such a rail is useful, for example, for providing a device that can be inserted into a body cavity and expanded, and then assembling the rail. An example of such a rail is described in US 2009/0076536 (Rentschler et al.) Optionally, the rail is configured for self-assembly, for example, provided as a plurality of fragments tethered to microfluidic channels. Optionally, the rail is configured as a plurality of fragments configured into an expandable canopy, for example, fragments anchored to the luminal sac wall configured for assembly upon expansion of the sac.

In one embodiment, the rail is an inflatable rail. An inflatable rail comprises a conduit made from a flexible material and is configured to become relatively turgid pressurized when filled with a fluid or when fluid flows through the conduit. In such an embodiment, the rail is flaccid when the conduit is not pressurized (not filled with a fluid) and becomes turgid upon pressurizing the lumen of the conduit, thereby forming a functional rail. In this configuration, the collapsed and flaccid state of the rail allows the rail to bend as needed while the device is maneuvered through a patient until it reaches the target site. When desired, the rail system can be inflated into its turgid state to provide support to railed devices such that the railed devices can move along the rail. Optionally, the rail comprises a fork in the conduit, wherein the form splits a single conduit into a plurality of conduits, wherein each of the plurality of conduits can support a railed device when turgid. Optionally, the fork comprises a control circuit configured to differentially control the flow of fluid from the single conduit into the plurality of conduits. In such a configuration, the user can choose which of the plurality of conduits to fill to turgidity and which to keep in their flaccid state. Optionally, the control circuit is a fluidic amplifier, for example, as detailed in U.S. Pat. No. 4,000,757 (Freeman). Such a rail is also useful outside of (without) an expandable device of the present invention.

In one embodiment, the rail is an inflatable rail embedded in or contoured against the sac wall. Optionally, the rail imparts rigidity to a flexible sac wall when the rail is inflated to turgidity.

In one embodiment, the rail is fluidic channel (e.g. microfluidic channel). Such a fluidic channel can be configured to provide hydraulic fluid. In one embodiment, the fluid is supplied in the wall of the sac through an expandable network of channels forming a rail network embedded in the wall of the sac as known in fluidics technology. The railed devices can, for example, comprise a protrusion that locks into the fluidic channel and is propelled by the fluid pressure.

In one embodiment, the rail is contiguous with the sac. Optionally, such a rail is embedded and/or formed as a mold with the sac (e.g. made of the same material as the sac). Optionally, the such a rail is made from a malleable material.

In one embodiment, the rail is discontiguous with the sac, for example, tethered to the sac at one or more locations.

In one embodiment, the device comprises a plurality of rails arranged longitudinally with respect to each other. Such a configuration can be used, for example, to provide different railed devices at different locations in an expandable sac, for example, to localize a tool (e.g. microrbt) at a specific segment of the expandable sac or to move (by tethered motorcar) a specific segment of the sac wall.

In one embodiment, the device comprises a plurality of rails arranged laterally (e.g. parallel) to each other. Optionally, each of the rails comprises a railed device tethered to a different portion of the sac wall, for example, portions of the sac wall that aren't in proximity to each other (e.g. opposite or parallel walls). Such a configuration is useful for example, to provide bends, curves, or articulations in wall segments of the device, or to impart a "wiggling" motion, i.e. curving or contracting one wall using movement of a railed device (tethered motorcar) on one rail, and then curving or contracting the other wall using movement of a railed device (tethered motorcar) on the other, laterally spaced rail). An example of such is detailed in Example 13.

In one embodiment, the rail is any rail that provides a support for securing a railed device there to and does not block a tool carried by the railed device from accessing the lumen (e.g. luminal wall) of the sac. Not included in this embodiment are rails that are themselves a contiguous enclosure (tube) through which a railed device and a tool (in its entirety) travel.

In one embodiment, the rail system comprises a railed device tethered to the sac wall ('tethered motorcar') and the rail is not attached to the sac wall at a location in close proximity to the tether on the wall (to allow movement of the wall segment at the tether to move about the rail along with the railed device).

Other useful rails are described, for example, in US 2009/0076536 (Rentschler et al.).

Tools

An expandable device of the present invention comprises an expandable sac comprising at least one tool. Optionally, the tool is carried by a railed device.

Useful tools according to the present invention include robots, diagnostic and therapeutic ('d/t') instruments, housekeeping tools that can be manipulated to move or shape a sac or sac component, stabilizing tools configured to stabilize another tool or hand-operated equipment, and tools that can deploy, modify, or assemble other tools or devices.

In one embodiment, one or more tools are fragmented or foldable. Fragmented tools are those whose parts can be configured together after disassembly to form a functional tool. Foldable tools are those which comprise parts that can be folded or collapsed on each other and unfolded or expanded to form a functional tool. Optionally, the tool is fragmented and configured for self-assembly. Optionally, the foldable tool is configured for self-unfolding as is known in the art. In such embodiments, the tools can be inserted into a patient transported to the target site as fragmented or folded tools and then re-assembled or unfolded at the target site. Optionally, the fragments of a fragmented tool are carried on different rails ('cooperating rails'), e.g. as described by Chung et al. ("Guided and fluidic self-assembly of microstructures using railed microfluidic channels"; Nature Materials 7, 581-587 (2008)). Optionally, cooperating rails position the fragments in proximity to each other for assembling.

In one embodiment, one or more tools are either attached to the wall of the sac or carried on a rail. A tool that is attached to the wall of a sac is optionally, attached via tether, adhesive, magnetic, mechanical or other attaching means for permanently or reversibly attaching tools or devices to the sac wall. For example, magnets (or other holding means such as clips) embedded in the sac wall can serve to hold or stabilize a metal toolbox in which a sharp tool (e.g. cutting blade) or volatile substance is segregated from the remainder of the sac lumen (e.g. until needed at a target site).]

In one embodiment, an expandable sac provides a protective cushion and/or protective envelope for one or more tools.

In embodiment, one or more tools (e.g. suction, irrigation, or electrical tools) are coupled to a flexible access tube of a sac for operation thereof. Such an access tube allows external equipment such as fluid pumps, power supplies, videos monitors, and the like, to be coupled to tools in the sac.

In one embodiment, one or more tools are delivered to or removed from the expandable sac through an access tube after the expandable sac has been positioned in body cavity.

In one embodiment, the sac comprises sensors (e.g. motion sensors), functional and/or structural units (e.g. filaments, piezoelectric filaments, magnets), expandable conduits and tracks, or pre-formed conduits and tracks, for example, embedded in the sac wall. [Reference: Kim et. al., Materials for multifunctional balloon catheters with capabilities in cardiac electrophysiological mapping and ablation therapy. NATURE MATERIALS j VOL 10 j April 2011 www.nature.com/naturematerials.]

Robots

In one embodiment, the device comprises a robot, for example, a microrobot. Typically, a robot comprises an arm or other component that is actuated along one or more axes, for example, linear axes or rotational axes (e.g. imparted by a pivoting arm). The robot can comprise a d/t instrument or other tool attached to the arm. Optionally, the robot comprises a transport mechanism for gross movement of the robot as a whole (e.g. is carried by a railed device) and an actuator for movement of only part of the robot such as an arm connected to an instrument or other tool. The invention contemplates the use of any known robots, microrobots, or parts thereof.

Useful robots include fully assembled robots, fragmented (and assembleable) robots, or folding (collapsible) robots.

The invention contemplates the use of robots having any mechanism for transport about the expandable sac device. Optionally, the robot is carried by a railed device. Alternatively, the robot can be transported by any other means, for example, wheels, walking components, or components for snake-like movements. Other useful mechanisms for robot transport are known in the art.

In one embodiment, the robot is a microrobot, for example, a robot with a cross-section of less than about any of: 4 cm, 3 cm, 2 cm, or 1 cm. Examples of useful micro robots are well known in the art, for example, as described by Forgione et al. [Surg Oncol. 2009 June; 18(2):121-9. Epub 2009 Jan. 14. "In vivo microbots for natural orifice transluminal surgery. Current status and future perspectives.]

In one embodiment, the robot is has cross-section of greater than about any of: 4 cm, 3 cm, 2 cm, or 1 cm.

In one embodiment, a robot (e.g. microrobot) is configured to perform any of the following functions: tissue removal, tissue biopsy, targeted drug delivery, carrier of a radioactive seed, ablation, cryoablation, thermoablation (e.g. using heating elements such as RF or ultrasonic heating elements), stenting, carrier of electrodes, sensing (e.g. oxygen), cutting device, probing device, or carrier of an implant. The robot (e.g. microrobot) can be a railed device or a non-railed device.

In one embodiment, the robot comprises a means for transportation. Optionally, the means for transportation of a robot (e.g. microrobot) comprises any of: propeller, cilia/flagellae, electromagnetic pump, jet pump, membrane propulsion (rapidly vibrating membrane), appendages for crawling, moving coil linear actuator, moving magnet actuator, electromagnet actuator, piezoelectric actuator, electrostatic actuator, or electrothermal actuator. Examples of useful transport mechanisms for robots (railed or non railed) include: helical propellers, traveling-Wave propulsion, and external magnetic field creation, for example, as described by Nelson et al. ("Microrobots for Minimally Invasive Medicine"; Annu. Rev. Biomed. Eng. 2010. 12:55-85). Other examples of useful transport mechanisms include vibrational structure and three legs, e.g. as described by Hou et al. ("Design and Fabrication of a Miniature Railway Vehicle"; World Academy of Science, Engineering and Technology 51 2009, p 49-53), and tethered or untethered MEMS (e.g. scratch drive actuator). Other examples of useful transport mechanisms include an array of prismatic joints, for example, as described by (Murthy et al. ARRIpede: An Assembled Micro Crawler; Nanotechnology, 2008. NANO '08. 8th IEEE Conference on; 18-21 Aug. 2008, pages 833-836), SMA-actuated segmented microrobot, e.g. as described in "Development of a biomimetic miniature robotic crawler" (Autonomous Robots, Volume 21, Number 2, 155-163) or fluidic rail systems, e.g. as described by Chung et al. ("Guided and fluidic self-assembly of microstructures using railed microfluidic channels"; Nature Materials 7, 581-587 (2008)). Any of such means for transportation can also be configured to transport the expandable device as a whole (i.e. globally).

In one embodiment, the expandable device comprises a fragmented robot or a folding robot (collapsible and/or articulated). Optionally, the fragmented robot is any of the following assembling types: key/keyhole or other latching, magnetic assembly, pull string assembly, chain-based or lattice based self-assembling robot. Other examples of fragmented robots are well known in the art. An example of a pull string assembling robot is detailed in Example 14. An example of a key/keyhole latch is described by Chung et al. ("Guided and fluidic self-assembly of microstructures using railed microfluidic channels"; Nature Materials 7, 581-587 (2008)). Other examples of fragmented robots are described, for example, by Stoy et al. ("Modular Robots: The State of the Art"; Proceedings of the IEEE 2010 International Conference on Robotics and Automation workshop 3rd of May 2010, Alaska, Ak., USA).

Useful microrobots that can be provided in an expandable device of the invention include those described by Nelson et al. ("Microrobots for Minimally Invasive Medicine"; Annu. Rev. Biomed. Eng. 2010. 12:55-85), and Cepolina et al. ("A family of corobotic surgical set-ups". Industrial Robot: An International Journal, 30(6):564-574, 2003 polypyrrole-gold bilayer based microrobots, e.g. as described by Jagar et al. ("Microrobots for Micrometer-Size Objects in Aqueous Media: Potential Tools for Single-Cell Manipulation; SCIENCE VOL 288 30 Jun. 2000).

Figure 11:
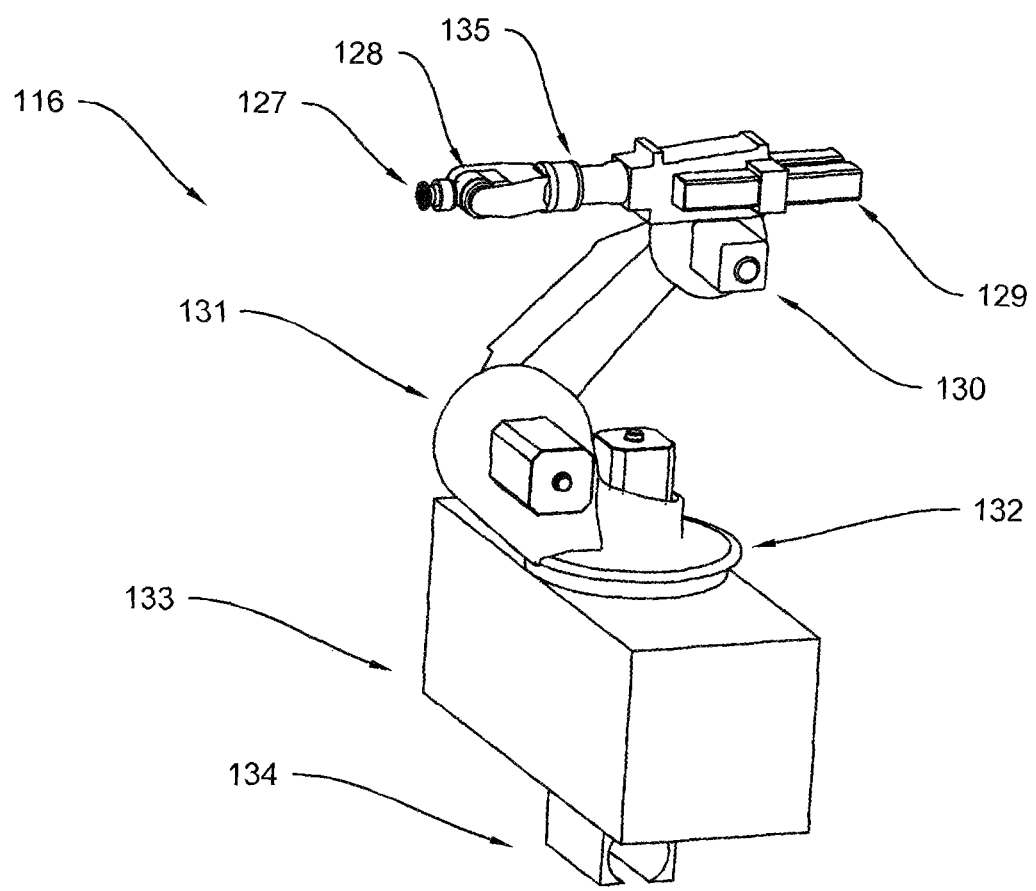
FIG. 11 depicts a robot useful in an expandable device of the invention.

A robot can have one or more actuators. FIG. 11 depicts a useful robotic railed device 116 comprising a rail coupler 134, a motor (one of three electromagnets) 133, a tool holder 127, and one or more actuators 128, 130, 131, 132 (rotational actuators), 129 (linear actuator).

Other useful microrobots include those used in microelectromechanical systems (MEMS).

Other useful robots and are described in US 2008/0058835 (Farrior et al).

Diagnostic and Therapeutic Instruments

In one embodiment, the device comprises one or more d/t instruments. Optionally, the instrument is a robotic device. Optionally, the d/t device is an actuated or non-actuated instrument. For example, the d/t instrument can be provided on an actuated (e.g. telescoping) arm configured to move the d/t instrument through a port and access the periphery of the sac. Additionally or alternatively, the instrument can optionally be actuated to perform micro-movements (such as closing of gripper jaws).

In one embodiment, the device comprises one or more diagnostic instruments selected from: a sensor (e.g. motion or light sensor), an imaging device, a camera, a stereoscope, an ultrasound sensor or imager, a light source (e.g. fiber optic), infra red, pressure (e.g. piezoelectric sensor) or temperature sensors, or MEMS sensors. Any of such instruments can be configured as robotic instruments and/or carried by a railed device. Alternatively, a diagnostic instrument such as in imaging device is not carried by a railed device.

In one embodiment, the device comprises one or more therapeutic instruments selected from: forceps, gripper jaws, an ablation tool, a cauterizer, a laser, a cryogenic ablation tool, a thermal ablation tool, an ultrasound ablation tool, a snare, a cutting tool, a microneedle holder, a needle drive, scissors, a sonic device, suction device, irrigation, a sawing tool, a boring tool, a fluid spraying device, a retraction tool, a stretching tool, a stapling tool, a puncture biopsy tool, a blunt dissection tool, a sharp dissection tool, a scooping tool, and a wiping tool. Any of such instruments can be configured as actuated and/or robotic instruments.

In one embodiment, the expandable device comprise a therapeutic tool selected from: radioactive substances healthy tissue, biological agents (e.g. living cells, bacteria, animals, worms, leaches, worms) or plant-derived substances. Optionally, the therapeutic tools is contained within an inner sac (e.g. ported inner sac) in the lumen of the outer sac.

In one embodiment, the expandable device is configured for suction and/or irrigation of body fluids (e.g. blood). Optionally, is suction is provided by an aspiration tube or a sponge in or on the expandable device. Optionally, the expandable device comprise and inner sac comprising an aspiration tube or sponge. Optionally, the expandable device comprises an outer sac comprising an aspiration tube or a sponge. Optionally, a is provided sponge external to an outer sac, e.g. it is an adjoining sac and/or is configured to be dragged along, absorbing the desired fluids from the abdominal space.

In one embodiment, one or more mini cameras (e.g. pill cams) and one or more lighting sources are embedded along an expandable sac wall (e.g. an outer sac).

Shaping and Movement Tools

In one embodiment, the device comprises one or more tools configured to be manipulated to move or shape an expandable sac or component thereof (housekeeping robot).

Examples of such tools include robotic arms (e.g. microrobot) and inner sacs that can be expanded to shape an outer sac.

Other examples include: structural units embedded in the wall of an expandable that sac can be employed to shape the sac. For example filaments, piezoelectric filaments, or. magnetized structural units (e.g. embedded in a sac wall) can be brought into contiguity using any means to move the walls or segments of wall of concentric or adjacent sacs. Alternately, conduits for fluid embedded in the wall of any of the expandable sacs can conduct fluid to given segment of the sac wall lending rigidity or structural stability to the targeted segment (e.g. when the conduits become turgid). Alternately, a small movable nozzle can function as a shaping tool when moved on a rail into proximity with a segment of a sac wall directing a stream of fluid against the luminal wall of the targeted segment thereby expanding the wall differentially from the non-targeted area. Alternately, filaments embedded in the sac wall can expand or contract or coalesce together when subjected to heat, light or other activators using for example a heat or light emitting device mounted onto a rail that is transported to the targeted segment of the sac wall. Expandable or assembled frameworks are also useful to impart shape to the sac(s).

Stabilizing Tools

In one embodiment, the device comprises one or more stabilizing or orienting ('stabilizing') tools configured to stabilize another tool or hand-operated equipment. In such an embodiment, the expandable sac device can be used to expand a body cavity and the stabilizing tool can be manipulated to orient the equipment for a given procedure. Examples of such stabilizing tools include an expandable sac configured to allow placement of hand-operated surgical equipment, for example, to aid a physician during a medical procedure such as a laparoscopic procedure. Such an expandable sac is optionally configured to expand to a volume that leaves a substantial void between the inner and outer sac to allow manipulation of the surgical equipment. Additionally or alternatively, a stabilizing tool comprises a plurality of stabilizing tools (e.g. sacs) configured to sandwich a hand operated equipment or other tool.

Expandable, assembled, or otherwise configured framework structures within the sac wall or lumen of the sac can also form desired cavity space and impart stability and orientation parameters for operation of the hand operated equipment or other tools.

Combinations of Tools

In one embodiment, the device comprises a combination of tools. Optionally, the combination includes any combination of robots, diagnostic and therapeutic ('d/t') instruments, shaping or movement tools, and stabilizing tools. Optionally, one or more of the tools (e.g. each tool of the combination) is carried by a railed device and/or a robot. Optionally, the d/t instruments that have moving parts are carried and/or operated by a robot (e.g. microrobot).

In one embodiment, the device comprises one or more diagnostic instruments and one or more therapeutic instruments. Optionally, the diagnostic and therapeutic instruments are robotic instruments and/or are carried by a railed device.

In one embodiment, the device comprises one of the following combinations of d/t instruments ('COMBOS'):

1. camera, lighting instrument, suction instrument, and irrigation instrument.
2. camera, lighting instrument, suction instrument, irrigation instrument, and forceps instrument.
3. camera, lighting instrument, suction instrument, irrigation instrument, forceps instrument, and cutting instrument.
4. camera, lighting instrument, suction instrument, irrigation instrument, forceps instrument, cutting instrument, and clip providing instrument.
6. camera, lighting instrument, suction instrument, irrigation instrument, forceps, cutting instrument, clip providing instrument and ultrasonic imaging probe device.
7. camera, lighting instrument, suction instrument, irrigation instrument, forceps, cutting instrument, clip providing instrument, ultrasonic imaging probe device and cryoablation instrument.
8. camera, lighting instrument, suction instrument, irrigation instrument, forceps, cutting instrument, clip providing instrument, ultrasonic imaging probe device and radiofrequency ablation instrument.
9. camera, lighting instrument, suction instrument, irrigation instrument, forceps, cutting instrument, clip providing instrument, ultrasonic imaging probe device, and cryoablation instrument or radiofrequency ablation instrument.
10. camera, lighting instrument, suction instrument, irrigation instrument, forceps, cutting instrument, clip providing instrument, ultrasonic imaging probe device, cryoablation instrument or radiofrequency ablation instrument, and retraction instrument.
11. camera, lighting instrument, suction instrument, irrigation instrument, forceps, cutting instrument, clip providing instrument, ultrasonic imaging probe device, ablation instrument (radiofrequency and/or cryoablation), retraction instrument and blunt dissection instrument.
12. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument and therapeutic substance application instrument (e.g. glue).
13. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue) and telescoping instrument fitted with any one or more of the instruments described above at its distal end.
14. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described above at its distal end and snaring instrument.

15. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described above at its distal end, snaring instrument and sewing instrument.

16. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described herein at its distal end, snaring instrument, sewing instrument and heating instrument.

17. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described herein at its distal end, snaring instrument, sewing instrument, heating instrument and sensing instrument (e.g., light, motion, pressure, or temperature).

18. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described herein at its distal end, snaring instrument, sewing instrument, heating instrument, sensing instrument (e.g., light, motion, pressure, or temperature) and clamp applicator instrument.

19. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described herein at its distal end, snaring instrument, sewing instrument, heating instrument, sensing instrument (e.g., light, motion, pressure, or temperature), clamp applicator instrument and hook instrument.

20. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described herein at its distal end, snaring instrument, sewing instrument, heating instrument, sensing instrument (e.g., light, motion, pressure, or temperature), clamp applicator instrument, hook instrument and speculum instrument.

21. camera, lighting instrument, suction instrument, irrigation instrument, forceps, cutting instrument, clip providing instrument, ultrasonic imaging probe device, ablation instrument (radiofrequency and/or cryoablation), retraction instrument, blunt dissection instrument, therapeutic substance application instrument (e.g. glue), telescoping instrument fitted with any one or more of the instruments described herein at its distal end, snaring instrument, sewing instrument, heating instrument, sensing instrument (e.g., light, motion, pressure, or temperature), clamp applicator instrument, hook instrument, speculum instrument and screw fixation instrument.

22. sensing instrument (e.g., light, motion, pressure, or temperature sensing instrument), used alone or in combination with other tools 23. camera (e.g. infrared camera) used alone or in combination with other tools 24. lighting instrument used alone or in combination with other tools Examples of uses for instrument combinations include:

COMBO #1 (from above): The expandable device in this configuration can be used, for example, to perform an explorative procedure, for instance to ascertain whether there is bleeding from the site of removal of a friable polyp during a colonoscopy in the large intestine of a patient with diminished blood clotting capacity. For instance, if the patient cannot undergo another colonoscopy, in this scenario, the expandable device is deployed by insertion into the rectum and from there it is propelled with its own means of mobility assisted by some antiperistaltic movement of the patient's colon, which contracts on the expandable device (one of its inner sacs being filled with a suitable fluid). Guided by a camera with illumination from a light source, the expandable device reaches the site of polyp removal. Sporadic cleaning of the transparent sac covering the camera is performed using the irrigation instrument that protrudes through a portal adjacent to the camera. Some blood is seen in the luminal wall of the colon at the target site and using the irrigation and suction instruments in adjacent portals, the blood is removed and the site is pictured for evaluation. The expandable device now moves in the reverse direction with its own mobility assisted by peristaltic movement of the patient's colon and is extracted from the rectum by forceps through a speculum.

COMBO #12 (from above) would be useful, for example, in a clinical situation involving an inflammatory disease and an ulceration on the wall of an ovary. Here, incisions or flexible scopes involving tissue trauma and manipulation could be relative contraindications. This expandable device, being soft and compressible, can be inserted by vaginal speculum upto the cervix from where it moves into the uterus and through a fallopian tube that has an ulceration. A special glue to apply on the ovary is available, but is too viscous for transport through the supply port of a flexible endoscope which lacks enough ports for one forceps to hold the capsule of glue which will be squeezed onto the ovary, another to dissect surrounding adhesions (scar tissue) and another to grasp the ovary and pull it away from the adhesions, not counting camera and light source.

The arrangement of sacs and movable railed instruments allows for an inner sac of the expandable device to contain a squeezable capsule with the glue. Once the main (outer) expandable device sac reaches the fimbrial opening, the inner sac moves out through a port (1) in the first sac wall toward the affected ovary. A camera is attached to the forward pole of the main expandable device sac.

Next, a blunt dissection instrument is moved by motor-on-rail mechanism adjacent to port (1) of the second sac and is used to dissect adhesions away from the ovary wall, after which it is withdrawn and the capsule, held by a forceps-like applicator instrument, is moved by motor-on-rail mechanism through a port (2) in the second sac adjacent to port (1) of the second sac. The applicator with capsule now outside port (2) of the second sac squeezes glue onto a segment of the ovary adjacent to the fallopian tube fimbria, after which it withdraws into the second sac through port (2).

A forceps instrument is then advanced through this same port (2) to bring the ovary away from the adhesions and closer to the fallopian fimbria. A second forceps instrument advances through port (1) to hold the fimbrial wall against the ovary while the glue sets (after the capsule applicator is withdrawn). After instruments are withdrawn through the ports, the expandable device moves in the opposite direction until it is withdrawn by forceps via a vaginal speculum.

In one embodiment, the device comprises a plurality of d/t instruments. Such a device can perform a plurality of functions or processes, for example, as required for a given medical procedure. Optionally, the device is configured to perform one of the following procedures, resection or partial resection, ablation, prostatectomy, coronary artery bypass; cutting away diseased tissue from sensitive parts of the body such as blood vessels, nerves, or important body organs or structures; gallbladder removal; hip replacement; hysterectomy; kidney removal; kidney transplantation; mitral valve repair; pyeloplasty (surgery to correct ureteropelvic junction obstruction); pyloroplasty; tubal ligation; removal of adhesions between organs and body structures; mucosal resection in lumens of various organs (e.g. in the sinus cavities); drainage of blood or abscess material from a variety of body tissues (e.g. the dura of the brain, the pleural space around the lungs); ligament repair; spinal disc repair; spinal ligament repair; spinal bone resection and repair; aneurysm repair; polypectomy. With the teachings provided herein, the skilled artisan will readily appreciate which tools are useful for incorporation into an expandable device to perform such procedures. In one embodiment, all of the tools are provided by the expandable device. In another embodiment, the procedures can be performed in cooperation with manual operative means and other manually operated instruments and devices and the expandable device only comprise some fo the required tools.

Movement

An expandable device of the present invention can be moved in any manner. In one embodiment, the expandable device as a whole is transported. In one embodiment, segments or portions of the expandable device is moved.

In one embodiment, the expandable devices is manually transported, for example, inserted into patient using a hand-operated instrument such as forceps. In such an embodiment, the expandable device is placed in the body cavity and then expanded, for example, to create a stabile work environment and/or organ retraction.

In one embodiment, the expandable device comprises a motorized means for movement (or 'means for global movement' of the expandable device). Optionally, the motorized means for movement is any of: an luminal motorized device tethered to a sac wall, a propeller (e.g. as detailed in U.S. Pat. No. 6,240,312), a linear actuator (e.g. pneumatic actuator, e.g. as detailed in U.S. Pat. No. 6,648,814), serially arranged inflatable chambers (e.g. as detailed in US 2010/0022947), an bracing (e.g. inflatable) member coupled with a linear actuator (e.g. as detailed in U.S. Pat. No. 5,337,732), a variable length extending segment (e.g. as detailed in U.S. Pat. No. 5,906,591), a pneumatic vacuum (e.g. e.g. as detailed in U.S. Pat. No. 5,906,591), a memory shape actuator (e.g. as detailed in U.S. Pat. No. 7,655,001), motorized wheels (e.g. as detailed in U.S. Pat. No. 7,126,303), walking legs (e.g. as detailed in WO2010/044053), magnetic locomotion (e.g. as detailed in US20070265496; EP1591057, US20070265496, or WO2005122866), a guide track and a drive mechanism for movement along the track (e.g. as detailed in WO2005/070310), or tractor treads (e.g. as detailed in U.S. Pat. No. 6,240,312).

In one embodiment, the motorized means for movement (or 'means for global movement' of the expandable device) comprises a motorized device tethered to the wall of a sac ('tethered motorcar'), for example, as detailed in Example 2, Example 3, and Example 13. Optionally, the motorized device is in the lumen of a sac of the expandable device. Optionally, the motorized device is a railed device (although non-railed microrobots can also be used to move a sac wall by tethering). Optionally, the motorized device is configured for inchworm movement (e.g. electromagnetic inchworm movement). Optionally, the expandable device comprise tethered motorcars configured to provide global movement of the device (i.e. the device as a whole), to spread the device out, or provide segmental movement (i.e. bending, articulation, or other localized movement of the sac wall), e.g. as detailed in Example 13. Optionally, the tethered motorcar is reversibly tethered to a sac wall (e.g. by retractable pylon). If the tethered motorcar is a railed device, the rail can be unfixed from the wall, reversible fixed to the wall, or fixed to the wall at a location remote from the tethered segment.

In addition, the means for global movement of the expandable device can be any means for moving robots or microrobots (e.g. as described herein).

Methods

In one embodiment, an expandable device of the present invention is used in a medical procedure requiring access to a body cavity, for example, to treat or diagnose a target site in or near the body cavity.

In one embodiment, the device is positioned and operated within a body cavity of a patient. Optionally, the device is inserted into the patient through a natural orifice. Optionally, the device is inserted through an incision. Optionally, the devices is first inserted into a first body cavity through a natural orifice and then inserted into a second body cavity through an incision made in the first body cavity, for example, as in a NOTES procedure.

For example, a small incision is made and the device is inserted through the incision in its collapsed state. The device can then be expanded, for example, to provide space within the cavity of a patient and various tools (e.g. housed by the device) are operated within the cavity to perform a medical procedures, including, for example, any procedure described herein or described in any publication cited herein.

In one embodiment, a device of the present invention is used as or used with a natural orifice translumenal endoscopic surgical device, such as a NOTES device.

The devices of the present invention can be used to perform procedures (e.g. NOTES procedures) that, until now, required the most skillful hands.

Procedure that can be performed with a present device, include, for example, laparoscopic reflux surgery, cholecystectomy, appendectomy, adrenalectomy, obesity surgery, and treatment of linguinal hernia.

In one embodiment, the expandable device is used in combination with other devices such as a flex endoscope.

Examplary medical procedures that can be performed by an expandable device of the invention include: resection or partial resection, ablation, prostatectomy, coronary artery bypass; cutting away diseased tissue from sensitive parts of the body such as blood vessels, nerves, or important body organs or structures; gallbladder removal; hip replacement; hysterectomy; kidney removal; kidney transplantation; mitral valve repair; pyeloplasty (surgery to correct uretero-pelvic junction obstruction); pyloroplasty; tubal ligation; removal of adhesions between organs and body structures; mucosal resection in lumens of various organs (e.g. in the sinus cavities); drainage of blood or abscess material from a variety of body tissues (e.g. the dura of the brain, the pleural space around the lungs); ligament repair; spinal disc repair; spinal ligament repair; spinal bone resection and repair; aneurysm repair; polypectomy.

The invention also contemplates the use of the present devices outside of the medical field, for example, in search and rescue operations in collapsed buildings where rigid instruments cannot maneuver through tight spaces and in which a present expandable device (e.g. possessing malleability and containing viscous fluids) can spread more easily into crevices or in diagnosis, maintenance and repair of tubular conduits as in plumbing pipes. As another example, an expandable device can be configured as a as toy, e.g. that is stimulating to the imagination and helps teach biological systems, robotics, materials science and other scientific concepts in an enjoyable manner Superior Properties:

Among other advantages, examplary devices of the present invention provide one or more of the following superior properties:
1. Safe access to a body cavity
2. Safe and stable transport of instruments to the body cavity
3. Excellent visualization and illumination to decrease disorientation
4. Superior suction/irrigation in a cavity
5. Superior maneuverability and triangulation of instruments.
6. Performs operations with smaller incisions
7. Expands a lumen or cavity without having to inject air into body cavity, which would normally have to be absorbed and can result in metabolic effects and exert pressure on body structures such as blood vessels.
8. Provides continuity between the device and a cavity wall having a target site Safe access to a body cavity is facilitated, for example, in those instances in which one body cavity (e.g. having a natural orifice; or the female reproductive organs including the fallopian tubes or other lumens) is used to allow access to another body cavity (e.g. the pelvic and abdominal cavities), for example, as in a NOTES procedure. While flexible endoscopes can be used to gain access to the abdominal cavity without need for incisions in the patient's body, the endoscopes have limited functional capabilities based on inherent elongated design of endoscopes and based on the number of portals through which tools can be maneuvered simultaneously; whereas the expandable devices of the invention can be configured to have any number of ports which serve to allow instrument access to the target site.

Safe and stable transport of instruments to the body cavity is facilitated by a number of optional features of expandable devices of the invention. For example, the expandable device can provide a cushion for tools housed therein. Further, the expandable device can comprise a plurality of compartments (e.g. different inner sacs) to separate the tools from each other and from the patient's body lumens in transit to a target site. As such, the expandable device can provide not only an envelope to maintain the instrument clean and sterile in a separate sac or chamber within a sac, but it can provide cushioning in the form of surrounding semi-viscous fluids and sacs that jostle each other when compressed and can slide past each other absorbing the compressive forces that the body exerts while in transit to the target location for the desired procedures. Additionally or alternatively, examplary expandable devices can have fragmented or folded tools (e.g. robots) that are provided in a collapsed configuration in route to the target site, thereby minimizing trauma to a body lumen. Once at the target site, the tools can be configured to function as needed (e.g. assembly of fragmented tools or unfolding of folded tools) because examplary expandable devices provide a housing and assembling means (e.g. cooperating rails or pull strings) for the tools. An examplary robot device also provides a work environment upon expansion that can be used, for example, to service a tool before, during or after the operative procedure if needed.

Excellent visualization and illumination is provided, for example, by expandable devices comprising one or more light sources and cameras which are either embedded in the sac walls, carried on railed devices inside transparent sac walls, or otherwise provided in the expandable sac. The expandable device can have multiple cameras to provide more than one or two points of view and allow, for example, for markers to be placed in the surrounding sac walls to serve as orientation markers in addition to micro-gyroscopes (e.g. known MEMS devices) to give additional feedback to the operating team members. An examplary expandable device can not only comprise and transport multiple sensory devices into the vicinity of the target location, but provides (e.g. upon expansion) for a stable platform/work environment to maneuver the sensors into position and/improve orientation and visualization.

Superior suction and irrigation in a body cavity or space is independently or collectively accomplished by a number of features of examplary expandable devices. For example, an expandable device can comprise suction and/or irrigation tools that can accurately be placed. Further, these tools can be attached to different "appendages" to extend the suction and/or irrigation tools outward in multiple directions to suction fluid or debris resulting from operative procedures. The "appendages" are, for example, evaginating sacs (e.g. inner sacs evaginating through ports in the outer sac), robotic arms (e.g. telescoping arms), or segments of the outer sac wall that can extend, e.g. by expansion of the sac wall (e.g. as in a malleable sac wall). These appendages can be used, e.g. for reaching and encompassing spaces in between body organs or tissues. In addition, multiple cameras and sensing devices embedded in the wall of the sacs or in the luminal cavity of the sacs can be provided detect the material to be suctioned. In addition, the incorporation of ports in an expandable sac wall can be used to release and retract sponges, aspiration tubes, or irrigation tools. Alternatively, an outer sac wall can contain a segment of absorbent material released from an invagination of the sac wall as formed, for instance, inside the space of an invaginated pleated segment of an outer sac wall.

Superior irrigation is accomplished, for instance, via one or more fluid expelling devices carried on a rail and protruding through ports in sac walls which can be maneuvered, e.g., with a change in shape of a sac wall or the movement of inner sacs themselves through portals in the outer sac wall of the expandable device.

Superior maneuverability and triangulation of instruments is provided, for example, by the ability to deploy a stable work environment or platform about which tools can move. For example, the expandable device can provide a framework or multiple frameworks on which moving tools are stabilized and, if desired, a base from which tools can exert the needed force against the target tissue. This can be used, for example, to accomplish any one of numerous operative procedures such as spreading apart or stabilizing tissue while it is being treated (e.g. sewn, cut etc). The expandable device also provides for precision movement of the d/t tools, for example, allowing only its desired moving parts (e.g. tissue-contacting members) to move in the manner in which it has been configured to perform a desired functional task. Another feature of examplary expandable devices that provides a desired maneuverability and triangulation is the use of expandable frameworks (e.g. "T" framework). Multiple, appropriately sized tools can be brought into close proximity to the target tissue allowing for simultaneous operations, e.g. retraction of tissue parts, clamping, cutting, irrigation and suctioning of fluids followed by clipping, suturing, cautery, suctioning of surgical smoke, cleaning the operative field and nearby cameras or tools using a water stream, irrigation of resultant fluids and so forth during commonly performed operative functions required in gall bladder removal, polypectomy, tubal ligation and numerous surgical procedures. Other examples of operative procedures in which an expandable device can provide superior maneuverability and triangularion are described in the literature for instance in Abe, N et al., (Single incision multi-port laparoendoscopic surgery . . . http://www.springerlink.com/content/h81h3133v808q6jv/fulltext.pdft). This article delineates how one flexible, multi port endoscopic tool performs a segment of gall bladder removal surgery. The expandable device, in this respect, can have multiple ports akin to the 3 or 4 ports available in the endoscopic tool. Whereas the endoscopic tool has a much smaller limit in number of port based on the diameter of the endoscope, the present expandable device can have many more ports that can be brought to bear on the performance of needed functions. Further, examplary expandable devices of the present invention are automated or semi-automated and do not require highly skilled hands to maneuver tools, as is required for endoscope-based procedures.

Superior maneuverability and triangulation is also imparted, for example, in a device comprising a segmented or localized embedded inflatable conduit and/or inflatable rail network which can be engorged with a suitable substance (e.g. fluid) which gives segmental rigidity, hence stability, to those local segments. At the same time, this allows for movement (e.g. articulation) in the sac wall that is between the rigid rail or conduit segment. Added articulation is one means of providing degrees of freedom to the entire sac, in addition to the articulations provided by the internal framework, when deployed. Hence the presence of inflatable conduits and/or rails can impart both segmental rigidity and articulation, enabling additional control for operative procedures.

Examplary expandable devices of the present invention can perform operations with smaller incisions, having the capacity of taking a minimal (collapsed) shape during entry through an incision in body tissues, e.g. the skin of a patient. This is achieved by, for example, the malleable or foldable nature of the sac walls and the capacity to empty a sac (e.g. through an access tube) of many or even all of its housed tools apart from structures (both pliable and semi-pliable) that are embedded in the sac wall(s). Numerous devices (e.g. tools or microrobots) can be introduced into the interior of the sac(s) (e.g. via access tube) after the initial sac has made entry into the desired body space (cavity, lumen or potential cavity). The devices can be introduced through the incisional space single file as fully assembled, folded, or fragmented tools.

Movement inside the body of a patient is also rendered easier by the capacity to maintain a compressed or thin profile while in the body, when moving or when immobile.

Examplary expandable devices of the present invention can expand a lumen or cavity without having to inject air into body cavity, which would normally have to be absorbed and can result in metabolic effects and exert pressure on body structures such as blood vessels. An examplary expandable device has the capacity to expand the sac walls in multiple directions, simultaneously to allow instruments or tools appropriate access to the body organs and tissues. This capacity can be achieved, for example, with more than one co-existing means, i.e. built-in redundancy. For instance, the means to expand a sac wall include: introduction and removal of fluids (e.g. gas, liquid, or semi-solid (g/l/s)) substances into multiple sacs in various quantities so as to achieve the desired expansion. Expansion can occur via introduction of fluids into any of multiple sacs in appropriately placed locations as already described. Expansion of sac wall(s) can also be achieved by introduction of the fluids into imbedded inner sacs or expandable conduits in the wall of an outer sac. Through the use of inner sac frameworks, malleable sacs, and/or tethered motorcars, a sac wall can be thus shaped to be contiguous to a body organ or tissue in its entirety (e.g. surrounding it) or in a segment of the organ or tissue, and thereby minimize or eliminate the need to transport a robotic device or tool far outside of the expandable device for the needed access to the tissue.

Examplary expandable devices provide continuity between the device and a cavity wall having a target site. For example, the use of a malleable sac can be used to deform a sac wall such that it is continuously positioned (e.g. contoured) against a cavity wall (e.g. a curved or irregularly shaped wall). Additionally or alternatively, expansion of the sac can occur in a segmented or localized manner, for example, in expandable devices comprising malleable sacs and/or tethered motorcars. Additionally or alternatively, segmental contiguity of the luminal contents of a sac(s) with an area of tissue can be achieved, for instance, by maneuvering (through a port in the outer sac wall) a second inner sac, which protrudes to the exterior surface of the outer sac expandable device, and is thus brought into contiguity with an area of tissue to which a substance is to be delivered that is contained in the inner sac). An adhesive (e.g. coated elastomer as described by Mandavi et al) introduced to the exterior aspect of the portal of the second/inner sac touching the target tissue provides a temporary seal to minimize or prevent leakage of the contents of the second/inner sac as they are brought into contact with the target tissue (by being sprayed, squeezed or otherwise released from a containing capsule). Hence, a desired material (e.g. therapeutic) is segregated from contact with any body tissues apart from the target tissue and after release to the target tissue leakage into the body (tissues or cavities) is likewise minimized or prevented. Examples of procedures that would benefit from this capability include: delivery of small amounts of expensive antibodies which should not be wasted, alpha emitting radioactive substances which should not be brought near healthy tissue, biological agents (e.g. living cells, bacteria, animals, worms, leaches, worms) or plant substances which can perform specific therapeutic functions to diseased tissue but should not be exposed to healthy tissue. In addition to delivery of special substances to a given tissue, the combination of these just described structural features allow for a contiguously placed port (e.g. sealed temporarily with adhesive) to enable more encapsulated evacuation of diseased tissue (e.g. cancerous cells) without allowing for contamination of any other body space or tissue. Suction tools on robotic devices can be maneuvered to this portal using for example the motorized railed devices. Thus, the diseased tissue is suctioned into an encapsulated space, such as an empty canister transported on a rail or else an inner sac.

The advantages of the invention can be combined with the complementary use of other surgical tools and methods. For example, in one embodiment, the a surgeon performs some activities with their hands, and a device of the present invention is used to provide expansion of the cavity (e.g. abdomen), illumination with light sources, visualization with imaging devices, fluid absorption/suction with a suction device, and irrigation with an irrigation device. Without the use of a device of the present invention, such a method would otherwise require a large incision in the abdominal cavity or multiple incisions.

The use of multilayer sacs arrangements allows compartmentalization of a variety of complementary functions and capabilities into one device. For example, the sacs can serve to contain and separate different processes if they should not be in contact with each other. The sacs can later expel their contents into a common area within or outside the expandable device.

The use of motors situated along different parts of the outer or inner sacs allows a variety of functions such as moving the sac or different portions of the sac in multiple directions and multiple planes in unison or at different intervals to allow shapes to be formed as needed and movements as need.

The use of malleable sacs allows compression or folding when the sacs are going through a tight space (e.g. incision into an inside the body or between organs in the abdominal or thoractic cavity).

The use of malleable sacs allows the external or internal sacs along with their internal contents and attachments to become compressed and to become filled with varying types and amounts of fluids and can facilitate various types of movement, including sliding squeezing, engorgement, and taking various shapes as required for the application in the body lumens and cavities. For instance, the use of malleable sacs provides capacity of the external or internal sacs to sustain physical forces that a) squeeze or pressed together, or against adjacent sacs or body structures (e.g. in sliding against lumen walls, body cavities, or internal organs, bending around lumen walls, body cavities, and in between internal organs); b) extend the sacs in the desired directions, c) configure the sacs in desired shapes. Preconfigured, contiguous expandable units of any shape can be selectively expanded to form desired shapes for specific purposes by having fluidic contents within one of the internal sacs flow into preformed or created spaces within another adjoining sac to create a space within the abdominal cavity. For instance, a rounded, smooth contoured, and deformable sac can be configured to much more easily pass through lumens and cavities in between organs, and other passages of the body (e.g. sinuses). The use of liquids/gasses or semisolids can also give a shape to the expandable device which could expand to allow lumens lined with smooth muscle to contract around the sac and push it along one direction or another. This naturally occurring process called peristalsis usually occurs in the GI tract.

The use of malleable sacs provides, among other advantages, a contouring device configured to shape around an organ to take on its exterior shape. This can be further facilitated by orchestrated movements of optional motorcars tethered to a sac wall (e.g. to impart bending).

Among many other superior properties, examplary expandable devices of the present invention aim to take advantage of various factors such as: 1) the properties of materials that render malleability or viscosity to expandable sacs, 2) specific means to shape and move such sacs, and 3) arranging sacs within each other to allow compartmentalization or separation of diverse functions while also allowing intercommunication among the sacs as needed. As a result of the integration of these exemplary factors, the platform device can perform procedures with remarkable cooperation of tools.

Shaping and mobility of the present device can be accomplished, e.g. through a network of tracks or rails coupled to movable components attached to the walls of the sacs, although other suitable means of imparting movement and shape to the sacs using fluidics technology are available. Intercommunication between the lumens of the sacs and the body cavity occurs via portals through which devices can move to other sacs or sacs themselves can move into other sacs or into the body cavity.

Examplary superior functions offered by a present expandable device include one or more of: shaping within, around, or inbetween body lumens, cavities and organs to bring diagnostic, therapeutic, and other functional devices, including micro robots, into close proximity to the target tissue while also enabling the retraction, interaction, supply, servicing and transportation in and out of the body of these devices along with targeted organs, tissues or fluids.

The citations provided herein are hereby incorporated by reference for the cited subject matter.

EXAMPLES

Example 1 Electromagnetic Inchworm Motor

Figure 7:
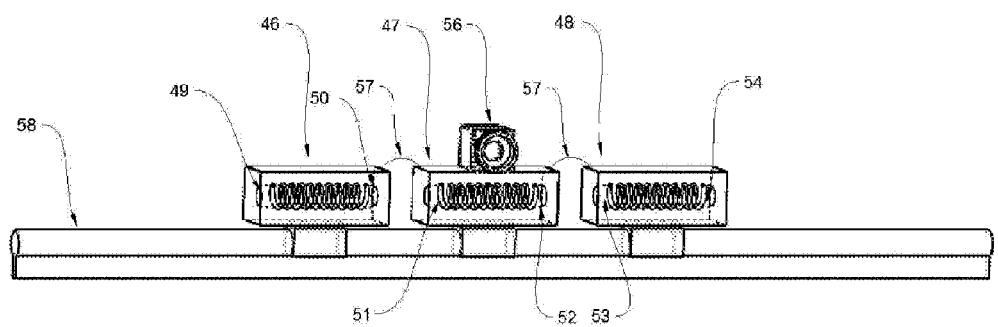
FIG. 7 depicts a motorized railed device coupled to rail, useful in a device of the present invention.

FIG. 7 depicts a railed device coupled to a rail 58. The railed device comprises an electromagnetic motor of the electromagnetic inchworm type. The railed device comprises a tool (camera) 56 mounted on a railcar 47. The inchworm motor comprises three railcars 46, 47, and 48, each comprising an electromagnet having poles, 49-50, 51-52, and 53-54, respectively. Each of the electromagnets is independently operable to control the charge at each pole and move the railed device by electromagnetic (attraction/repulsion) forces. Although the distance between railcars can be controlled by precise operation of the electromagnets, a distance limiter such as cable 57 is optionally provided to restrain the electromagnets from moving out of range of each other (for electromagnetic interaction). The electromagnets can be operated in any manner that imparts movement of the railed device about the rail 58.

As an alternative to providing each railcar with two poles, the railcars can have a single pole. As another example, the leadcar 46 and trail car 48 can each contain a single pole to interact with the intermediate car 47, which can contain two poles 51 and 52 to interact with the lead car and trail car, respectively.

Optionally, the electromagnetic inchworm motor is provided as a railed or non railed device and need not carry any particular device (such as the depicted camera). The electromagnetic cars will function as long as the electromagnets are arranged substantially collinearly. The "collinear"

arrangement can be strictly collinear (head to toe) or functionally collinear, i.e. the electromagnets are arranged to interact with each other by repulsion and attraction.

Surprisingly, such an electromagnetic inchworm motor can translocate a device, even without means to transiently stabilize or break a rail car (or car) such as a friction break or a clamp or other breaking device.

Example 2 Movement of an Electromagnetic Inchworm Motor

A railed device comprising an electromagnetic motor (e.g. as in Example 1 and FIG. 7) can be moved in an inchworm fashion by step-wise operation of electromagnets, as detailed in FIG. 6. The railed device comprises electromagnet railcars 46, 47, and 48, each comprising poles, 49-50, 51-52, and 53-54, respectively. The railed device optionally comprises a distance limiter such as membrane 55.

The railed device motor is configured to move the railcars in the following states:
1. Idle state: the electromagnets are charged such that no cars move
2. Lead car advance state: the lead car 46 advances by repulsion from intermediate car 47;
3. Intermediate car advance state: the intermediate car 47 advances by attraction to lead car 49 and/or repulsion from trail car 48.
4. Trail car advance state: the trail 48 advances by attraction to intermediate car 47.

The railed device can be moved in the opposite direction by reversing the steps. Each moving step or state is imparted by selecting an appropriate combination of charges on the electromagnet railcars that provides the desired state. Although numerous charge combinations exist that can provide each moving step or state, FIG. 6a through FIG. 6g depict one method for moving the railed device in an inchworm manner, wherein each step requires the modulation (changing) of only a single car's electromagnet(s). This is achieved by providing a railed device with rail car weights as follows: the weight of the intermediate car is less than the lead car and less than the trail car; the weight of the lead car is less than the combined weight of the intermediate and trail car; and the weight of the trail car is less than the combined weight of the intermediate and lead car (where "weight" is the object's resistance to motion).

Figure 6A:
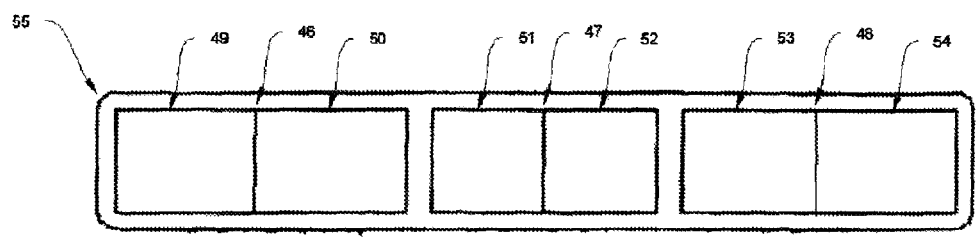
FIG. 6A through FIG. 6G depict an inchworm type electromagnetic motor useful in a device of the present invention.

FIG. 6a depicts the idle state in which poles 50 and 53 are negative and intermediate car 47 is neutral or positive.

Figure 6B:
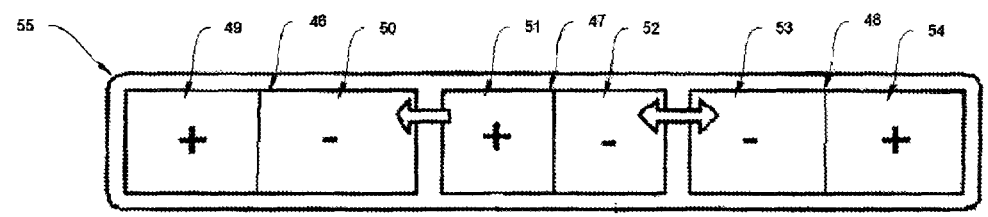

To advance the intermediate car, as depicted in FIG. 6b, the electromagnet(s) on the intermediate car 47 is modulated to provide front pole 51 with a positive charge (attracting to lead car 46) and rear pole 52 with a negative charge (repelling from trail car 48). Intermediate car 47 weighs less than lead car 46 and trail car 48. Accordingly, the electromagnetic forces move the intermediate car rather than the lead or trail car.

Figure 6C:
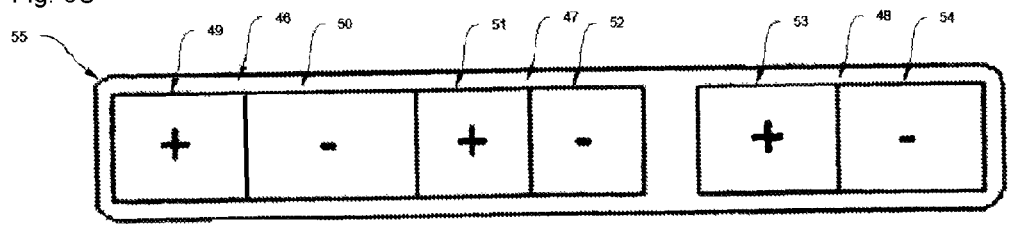
Figure 6D:
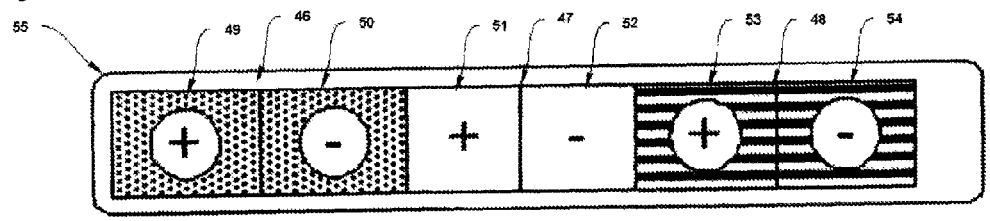

To advance the trail car, as depicted in FIG. 6c and FIG. 6d, the electromagnet(s) on the trail car 48 is modulated to provide front pole 53 with a positive charge (attracting to intermediate car 47). Trail car 48 weighs less than lead car 46 and intermediate car 47 combined. Accordingly, the electromagnetic forces move the trail car 48 rather than the lead or intermediate car.

Figure 6E:
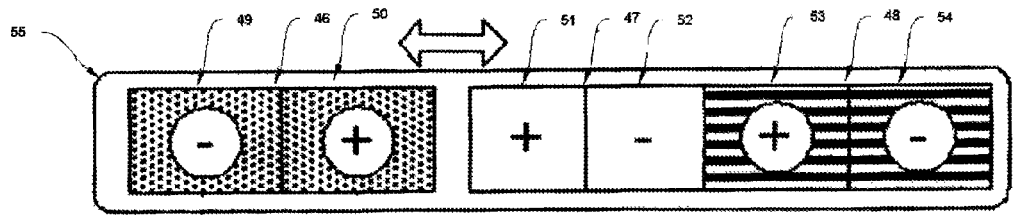

To advance the lead car, as depicted in FIG. 6e, the electromagnet(s) on the lead car 46 is modulated to provide rear pole 50 with a positive charge (repelling from intermediate car 47). Lead car 46 weighs less than intermediate car 47 and trail car 48 combined. Accordingly, the electromagnetic forces move the lead car 46 rather than the trail or intermediate car.

Figure 6F:
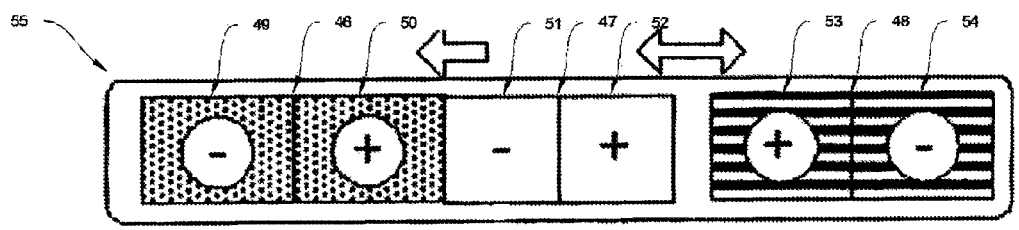

To advance the intermediate car, as depicted in FIG. 6f, the electromagnet(s) on the intermediate car 47 is modulated to provide front pole 51 with a negative charge (attracting to lead car 46) and rear pole 52 with a positive charge (repelling from trail car 48). Intermediate car 47 weighs less than lead car 46 and trail car 48. Accordingly, the electromagnetic forces move the intermediate car rather than the lead or trail car.

Figure 6G:
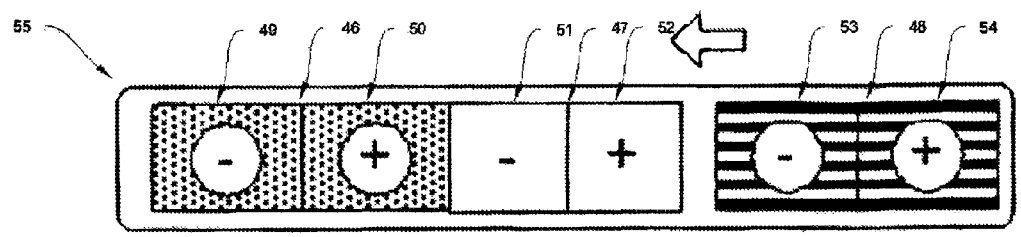

To advance the trail car, as depicted in FIG. 6g, the electromagnet(s) on the trail car 48 is modulated to provide front pole 53 with a negative charge (attracting to intermediate car 47). Trail car 48 weighs less than lead car 46 and intermediate car 47 combined. Accordingly, the electromagnetic forces move the trail car 48 rather than the lead or intermediate car.

Optionally, the electromagnetic inchworm motor is provided as a railed or non railed device and is useful even outside (without) expandable devices of the invention. The electromagnetic cars will function as long as the electromagnets are arranged substantially collinearly. The "collinear" arrangement can be strictly collinear (head to toe) or functionally collinear, i.e. the electromagnets are arranged to interact with each other by repulsion and attraction.

Surprisingly, such an electromagnetic inchworm motor can translocate a device, even without means to transiently stabilize or break a rail car (or car) such as a friction break or a clamp or other breaking device.

Example 3 Sac with Railed Device

FIG. 1 depicts an embodiment of the present invention. The device comprises an expandable sac 1 having a flexible access tube 2 for filling the sac with a fluid, thereby expanding the sac. The access tube may also be used for clearing or collapsing the sac. The device comprises one or more railed devices 3 which carry tools (e.g. robot or camera) and/or are tethered or attached to portions of the sac wall for movement thereof.

The sac wall comprises one or more portions 5 which are malleable to provide expandability of the sac at that portion 5. The entire sac wall can be malleable and can also have various portions with different malleability to provide differential expandability. A one or more railed devices (e.g. motorized railed devices) can be tethered to the sac wall to move (e.g. push or pull) the sac along an axis or along multiple axes simultaneously. Alternatively, a plurality of railed devices can be tethered to the sac wall to pull the sac along multiple axes, for example, simultaneously. In this example, the device can be configured to spread itself out. By selecting a sac with an appropriate design and malleability the tethered railed devices can be arranged and configured to predominantly move the sac about one axis, thereby moving the entire device in one direction while also being able to spread out in other directions. With the appropriate selection of sac and railed device arrangement, the device can also be configured to form different shapes, e.g. cavitations, encircling, or pincher-like movement, etc. in order to execute desired functions.

In addition to using solid, gaseous, or semi-solid substances to achieve expansion, the access tube configured and used to introduce/remove devices such as mini or micro robots pushed or suction with air or fluid or with a plunger type device.

Example 4 Multilayered Device with Ports

FIG. 2 depicts an expandable device of the invention. The device comprises an outer sac 6 having one or more malleable portions 13. Additionally, the entire sac can be malleable and/or can have portions with different malleability to provide differential expansion. The outer sac 6 comprises a port 14 (e.g. a valve) configured to provide a fluid-tight enclosure when the port 14 is closed and allow access to the periphery of the sac 6 when the port is open, for example, to allow a tool housed by the sac 6 access to a target tissue in a body cavity.

Figure 2A:
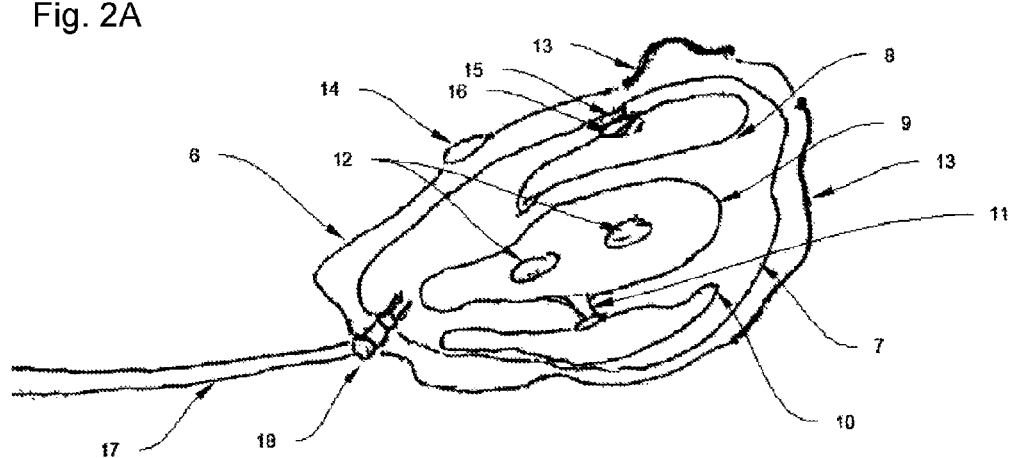
FIG. 2A and FIG. 2B depict a multilayered device of the present invention comprising ports.
Figure 2B:
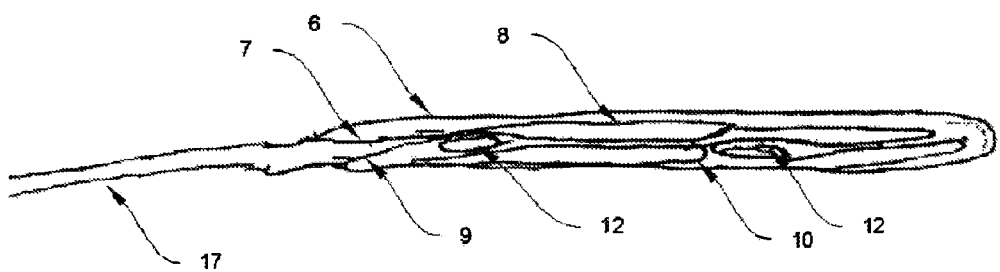

The device further comprises intermediate sac 7 (an inner sac) in the lumen of outer sac 6. The intermediate sac 7 comprises a connection 18 to access tube 17 for filling and/or clearing the sac 7 of a fluid to provide expansion and/or collapsing to modulate the volume of the device. The device transitions from the collapsed state, as depicted in FIG. 2b, to the expanded state, as depicted in FIG. 2a, by filling the intermediate sac with a fluid. Like the outer sac 6, the intermediate sac 7 comprises a port 15 providing access to its periphery. The intermediate sac 7 is useful, for example, to allow fluid/gas/liquid/solid or semi-solid substances to be received and/or to serve as a holding chamber for suctioned fluid or tissue from the body.

The device further comprises inner sacs 8, 9, and 10 in the lumen of the intermediate sac 7.

Inner sac 8 comprises a port which can be configured for transient or permanent alignment with port 15 of intermediate sac 7, which can itself be configured to align with port 14 of outer sac 6. In this configuration, a tool housed by inner sac 8 (not depicted in the figure) has access to the periphery of outer sac 6, for example, to contact a target tissue in a body cavity.

Inner sacs 9 and 10 are connected by a connecting sac 11. Inner sac 9 contains tools such as microrobots 12 for performing a desired function. This configuration provides, for example, expansion or expansive capability if a tubular segment is not available or if a sealed chamber is needed, for example, if sac 7 is filled with a fluid which should not enter either of the adjoining sacs.

Sac 8 may contain, for example, something other than a robotic tool, for example, a folded layer of artificial membrane that will be delivered for placement on a diseased body organ, e.g. a blood vessel wall. Sac 9 can then be used, for example, to house the robot(s) that can be used to remove the membrane from sac 8. Although a robot and a delicate material (e.g. artificial membrane) can be housed in the same sac, compartmentalization of the two protects the delicate material, during transport through tight spaces in the body, wherein the robots could otherwise pierce the delicate membrane. Further, the viscous fluid can be filled in sacs 7 and 9 could be act as cushions protecting both the membrane and the robots from compressive forces and from contact with each other.

Such a device with multiple inner sacs provides compartmentalization of complementary processes/instruments. This is especially useful when the processes/instruments should be separated, i.e. not in direct contact with each other. As one example, radioactive substances can require that a specified protective parameter be maintained at all times until delivery into a target tissue. The availability of a separate sac which can be maintained at a specific volumetric configuration facilitates this requirement.

Example 5

Multilayer Sac with Railed Device

Figure 3A:
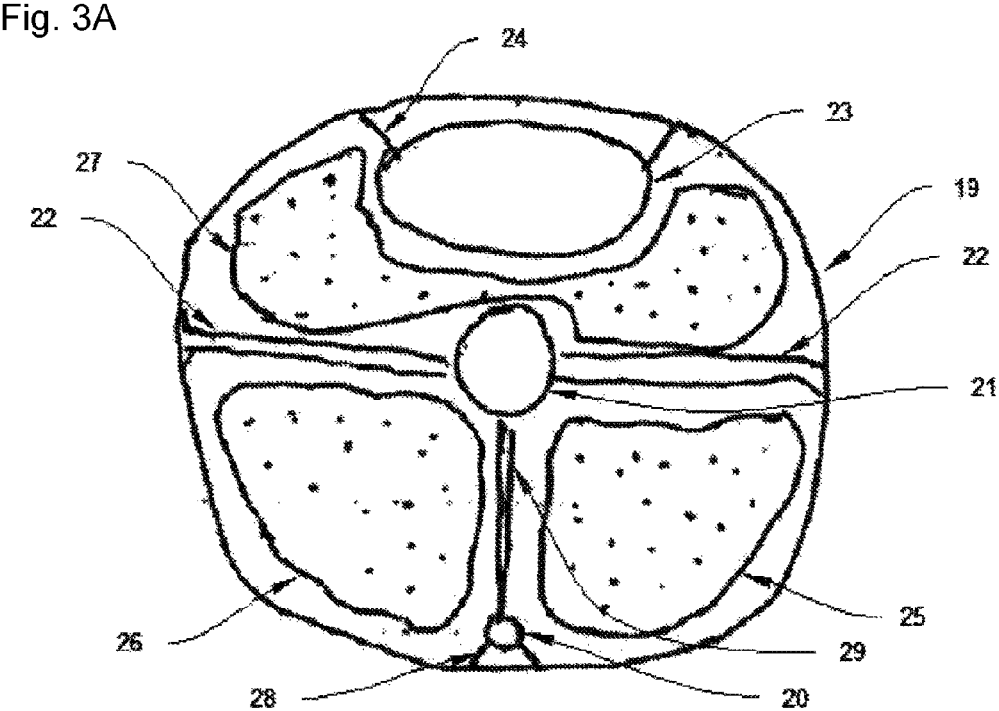
FIG. 3A and FIG. 3B depict a device of the present invention.
Figure 3B:
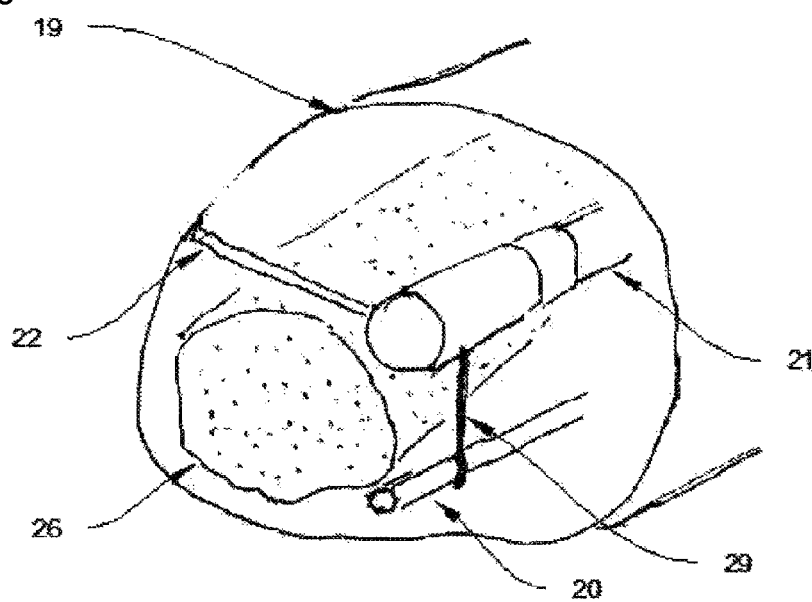

FIG. 3 depicts a device comprising an outer sac 19 having a rail 20 mounted by rail support 28. FIG. 3a is a cross-sectional (front) view while FIG. 3b is a perspective view (note that several parts are not depicted in the perspective view). A railed device 21 (e.g. with motor) is coupled to the rail 20 by railmount 29 and is tethered to the outer sac 19 by tethers 22. In this configuration, the railed device 21 acts as a motor car, using the tethers 22 to moving the outer sac.

The device further comprises a first inner sac 23 comprising a diagnostic device (e.g. camera) or other instrument. The sac 23 can optionally be attached to the outer sac (or other sac) by attachment points 24. The sac can be filled with a gas or other fluid to impart volume there to, for example, to stabilize the sac and diagnostic device (e.g. camera) as well as to protect the diagnostic device from contact with the outer sac and/or body cavity.

The device further comprises one or more second inner sacs 25 and 26 with access tubes (not shown) and can be filled with a gel or other fluid to impart shape and volume to the device.

The device further comprises a third inner sac 27 having an access tube (not shown) and can be filled with a viscous (thick and/or cushioning) fluid or other fluid.

Among other advantages, filling with a fluid can provide cushioning of the railed device (or other components) from compression by body structures and from an instrument (or other tool) contained in sac 23 and cushioning of the instrument from same (body structures and rail). In examplary expandable devices, as the sacs slide against each other, this facilitates squeezing of the entire platform through tight spaces without causing undue trauma against the adjacent body tissues or organs. Through optional ports or valves (some of which can be configured with small openings even when in the opened position), not depicted in this figure, very small amounts of viscous fluid (when the sacs are configured to contain such fluid) can be squeezed out when the sacs are compressed producing lubrication between the sacs, thereby facilitating squeezing and spreading movement of the entire platform. These same fluids can make their way into the luminal space of the outer sac 19 and into the body through similar ports in the wall of the outer sac 19 serving as lubricant for the entire platform as it moves, when this is needed

Example 6 Multilayer Device with Framework

Figure 4:
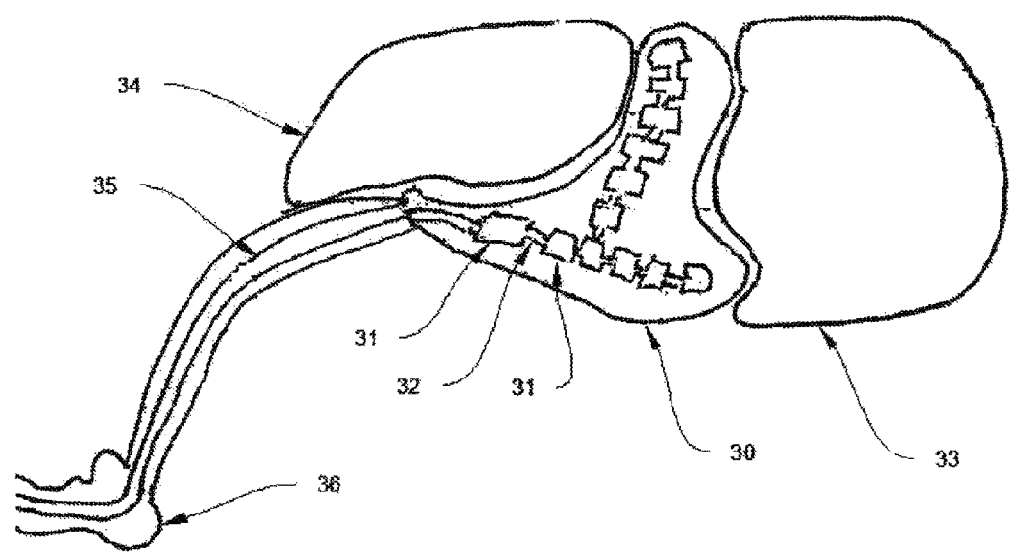
FIG. 4 depicts a multilayered device of the present invention comprising an expandable framework.

FIG. 4 depicts a device comprising an outer sac 30 and en expandable framework comprising a plurality of expandable sacs 31 connected by junctions 32. The framework can be fluidly connected to a fluid pump by access tube 35.

In one embodiment, the junctions 32 are tubes connecting the sacs 31 such that the sacs 31 are fluidly connected. Alternatively, the framework can be configured as a disassembled framework comprising a plurality of sacs 31 which comprise self-assembly elements to assemble at junctions 32.

In one embodiment, the device comprises means for expansion of the outer sac at a junction 36 at a location remote to the framework (e.g. second inner sac or another expander).

An "L" or a "T" shaped framework can be used, for example, to expand and provide a working space (e.g.

between two organs 33 and 34) while also providing a stabilizing member (e.g. the top portion of the "T"), as depicted in FIG. 4.

In one embodiment, the device comprises means for movement of an inner sac through a port (port not depicted) in the outer sac 30 near the juncture 36. The means for movement of an inner sac can be any of: a robot, an actuator, pneumatic device, or other means.

Example 7 Multilayered Device

Figure 5A:
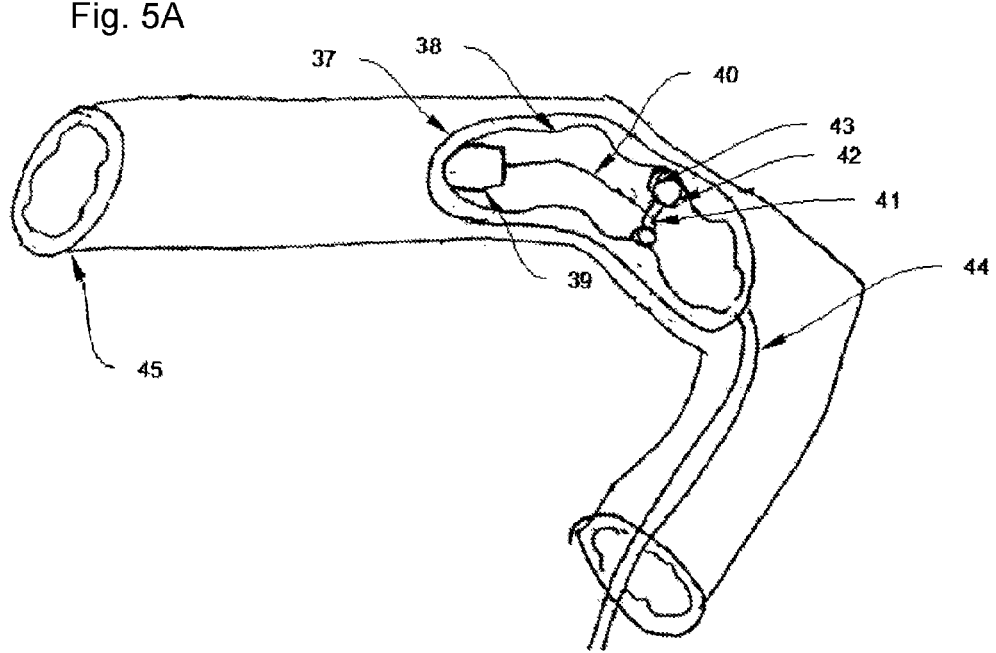
FIG. 5A and FIG. 5B depict a multilayered device of the present invention comprising a tool.

FIG. 5 depicts a device comprising an outer sac 37 and an inner sac 38 in the lumen of the outer sac 37. In the lumen of the inner sac 38 is a railed device comprising a camera 37 coupled to rail 40.

Parts 41, 42 and 43 are optional parts of the expandable device, such railed devices capable of traveling along the rail 40 which is configured (e.g. by expansion) to span the opposing luminal walls of the inner sac 38 e.g. in performing functions requiring contact with a concentric surface of the luminal wall as the device and/or the platform advance, such as in ultrasound scanning of the circumferential luminal wall of the intestines.

The space between the outer wall of inner sac 38 and the luminal wall of outer sac 38 can be filled with a fluid (e.g. gas, liquid, or gel, for instance gel used for ultrasound transducers functioning or cushioning).

The device is optionally inserted into the colon 45 and travels there through as it images the colon wall. The device can travel, for example, by muscle contraction (e.g. peristalsis, retro-peristalsis, or electrical stimulation).

Figure 5B:
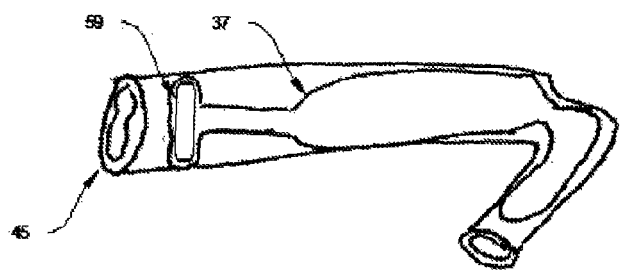

As depicted in FIG. 5b, the device can optionally comprise an inner sac 59 configured to expand in the colon. This can be used for stabilization or movement of the expandable device. For example, expansion of the inner sac can be used for anchoring one or more segments (portions) of the device against the walls of the lumen, a body cavity, or adjacent organs in the body.

Example 8 Multilayer Device

FIG. 8a depicts an expandable device of the invention.

The device comprises an outer sac 105 (FIG. 8b) and an inner sac (FIG. 8c) in the lumen of the outer sac 105. One or both sacs have their lumen in fluid connection with an access tube. For example, outer sac 105 can have its lumen in fluid connection with access tube 107 and inner sac 106 can have its lumen in fluid connection with access tube 108

The outer sac 105 has a rail 109 mounted to its luminal wall and a port 110 in proximity to the rail 109 such that a robot arm (robot not shown) can pass through the port 110 when coupled to the rail 109. Alternatively, the port 110 can be sized to allow a target tissue to pass through and protrude into lumen of the outer sac 105 such that a rail-mounted robot can interact with the tissue.

The device is optionally configured such that expansion of outer sac 105 is imparted by filling inner sac 106 with a fluid through access tube 107. The inner sac 106 can optionally be configured as a network of smaller sacs 111 fluidly connected by junctions 112.

The port 110 can optionally be configured as a valve such as a self-sealing valve. The self-sealing valve can be configured, for example, as an elastic member having slits 126 that can open, allowing a device (e.g. robot) to pass the valve and reseal upon retraction of the device back through the valve. as depicted in FIG. 8d.

Example 9 Multilayer Device

FIG. 9 depicts an expandable device comprising an outer sac which may be used in combination with of the depicted inner sacs. The device comprises an outer sac 113 and an inner sac 118, as depicted in FIG. 9c.

Figure 9A:
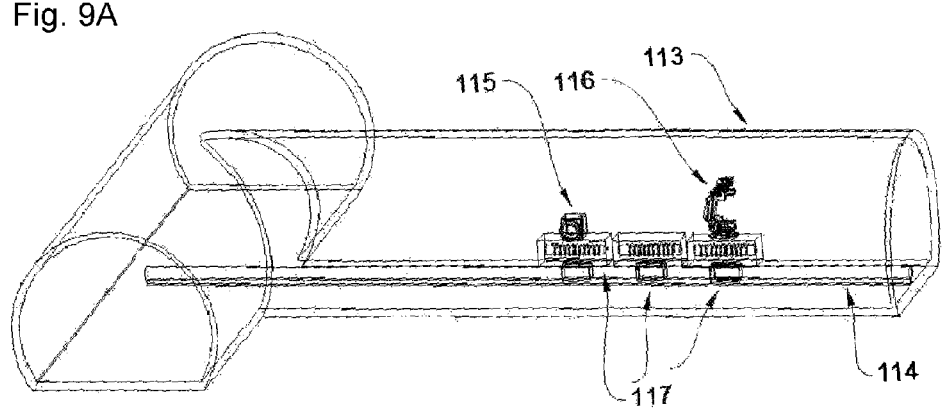
FIG. 9A through FIG. 9E depict embodiments of an expandable device of the invention.

As depicted in FIG. 9a, a rail 114 is mounted to the luminal wall of the outer sac 113 and one or more d/t devices or other tools such as camera 115 and robot 116 are coupled to the rail 114 as railed devices. The railed devices optionally comprise a motor such as a motor with three electromagnetic rail cars 117. Although the d/t devices 115 and 116 are shown as mounted on the motor railcars 117, these devices can alternatively be coupled to the rail on independent rail cars and pushed or pulled by the motor railcars.

Figure 9B:
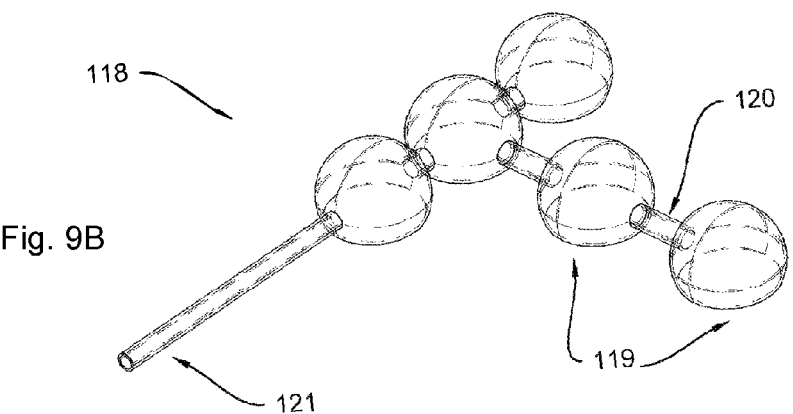

As depicted in FIG. 9b, the inner sac 118 can comprise a plurality of smaller sacs 119 with lumens fluidly connected to access tube 121 and fluidly connected by junctions 120 (e.g. tubes) to provide an expandable framework. Optionally, the inner sac 118 is in the shape of an "L" or "T", as depicted, for example, to create a working space between two organs while providing stabilization in a similar manner as described in Example 6. Optionally, the outer sac is malleable and configured to remain expanded upon deflation of inner sac 118.

Figure 9C:
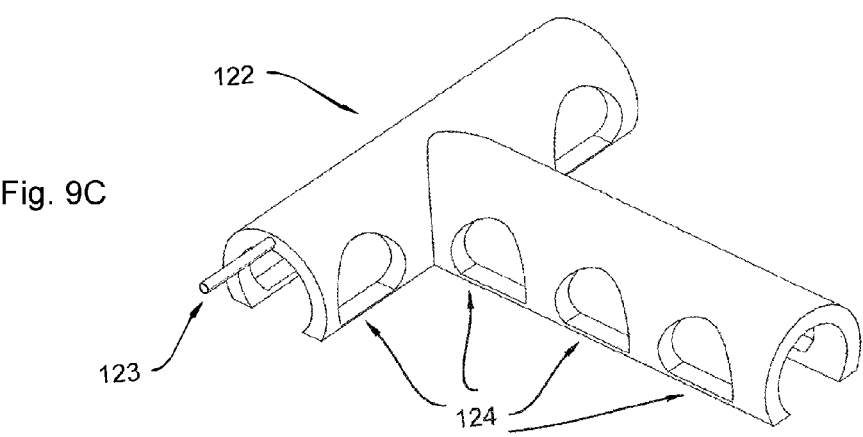
Figure 9D:
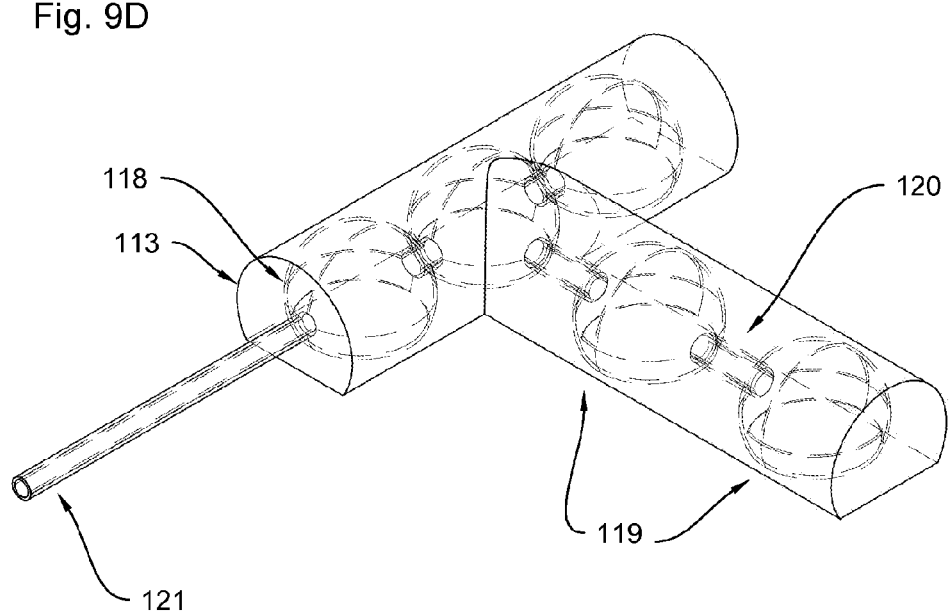
Figure 9E:
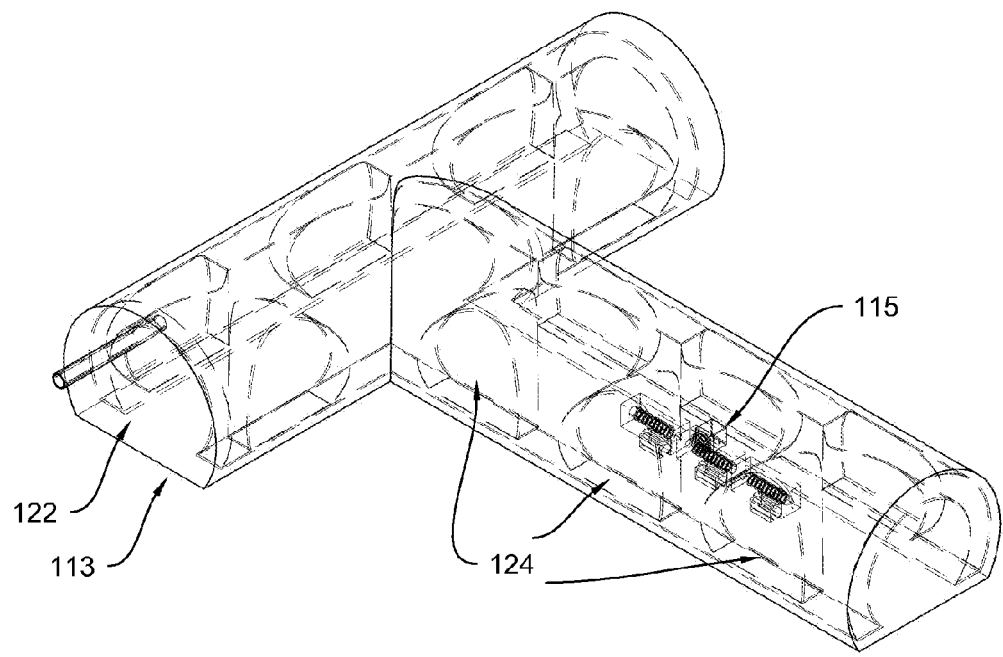

As an alternative to the expandable framework of inner sac 118 depicted in FIG. 9b and FIG. 9c, the device can comprise inner sac 122 which is formed as a bilayer defining a thin lumen in fluid connection with access tube 123, as depicted in FIG. 9d. The inner sac 122 is configured with windows 124 through the bilayer such that inner sac 122 can remain expanded while the railed device 115 moves along the rail, as depicted in FIG. 9e.

Example 10 Budding Segment

Figure 10A:
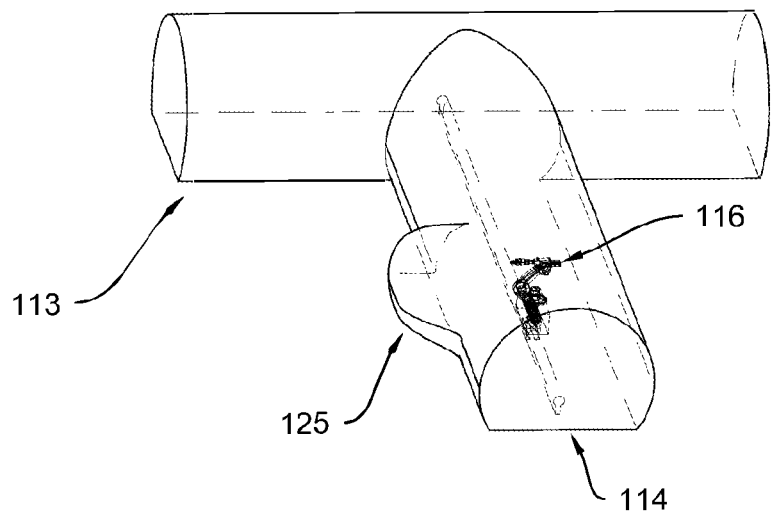
FIG. 10A and FIG. 10B depict an expandable device of the invention.
Figure 10B:
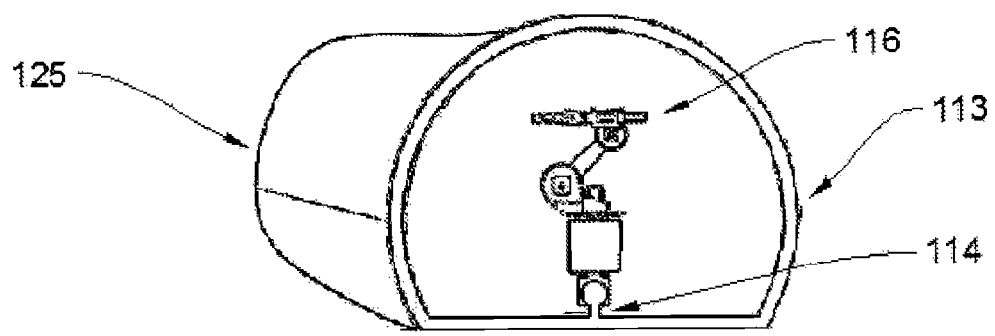

In one embodiment, an expandable device (e.g. multilayer device) comprises a segment configured for budding out, as depicted in FIG. 10. The sac (e.g. outer sac 113, as described in Example 9) comprises a segment 125 configured for budding out. The segment 125 can be configured for budding out by any manner. For example, the segment 125 can be a malleable segment such as a segment made from a memory shape plastic. Alternatively, if the sac is malleable as a whole then segment 125 can be a thinner walled segment that provides greater flexibility. Alternatively, the segment 125 can be configured as a bundled segment bound by a temporary clip.

The segment 125 can be induced to bud out, for example, by fluid pressure or by manipulation (e.g. pushing) with a robot.

Such a budding segment provides a superior working environment for target sites that are secluded in smaller cavities (e.g. diverticula) in the walls of a larger cavity or other small openings that the entire expandable device cannot fit within.

Example 11 Expandable Device

Figure 12A:
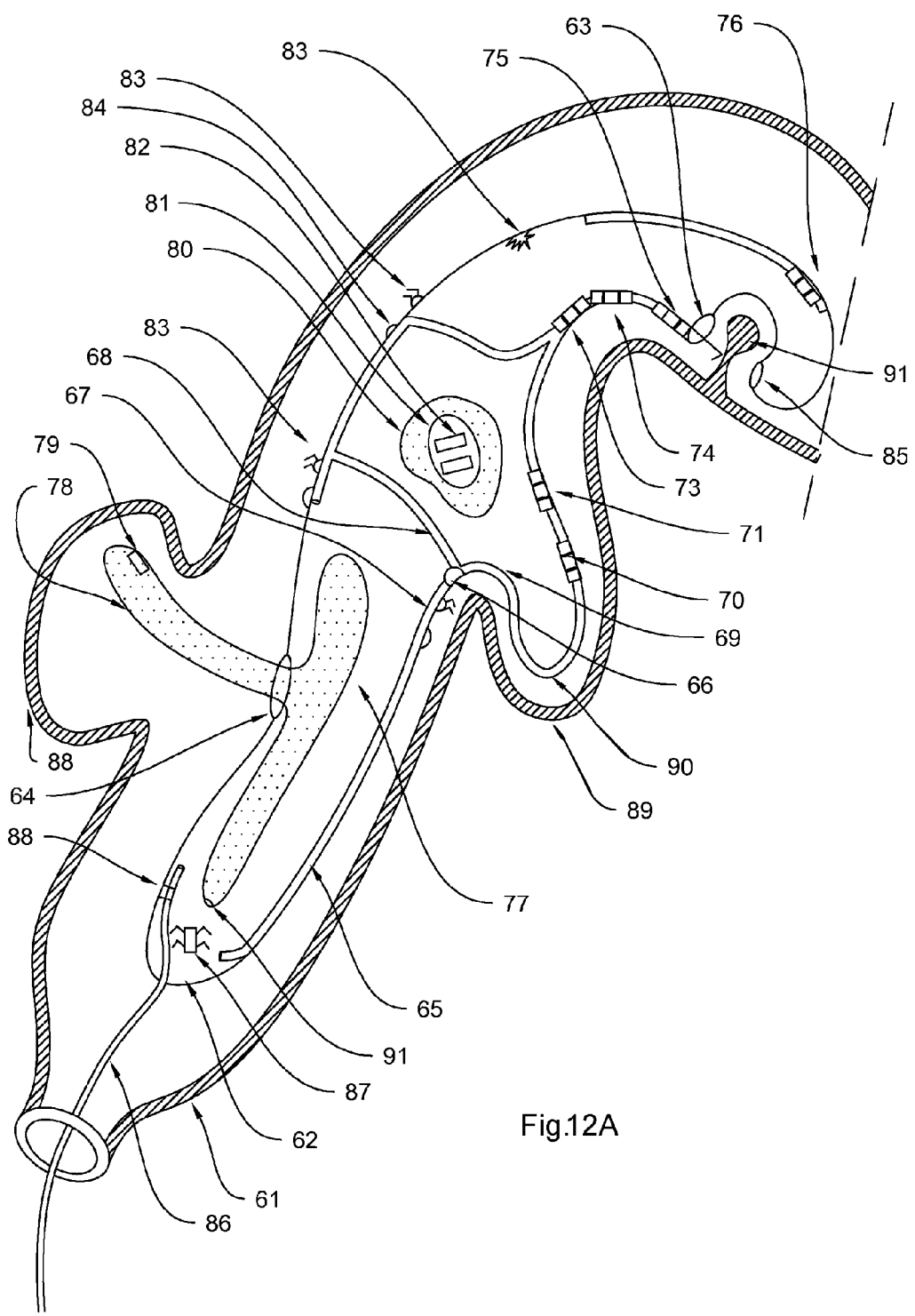
FIG. 12A depicts an expandable device of the invention.

FIG. 12 depicts an expandable device of the present invention. FIG. 12a depicts the entire device while FIG. 12b through FIG. 12f depict zoomed views of several optional components of the expandable device.

As a non-limiting example of a body cavity, the device is shown in the lumen of a sigmoid colon 61 (FIG. 12a).

The device comprises:
a. an outer sac 62;
b. one or more ports 63, 64;
c. a rail 65;
d. one or more railed devices 70, 71, 72, 73, 74, 75, 76;
e. one or more inner sacs 77, 80, 81;
f. one or more robots 82, 87
g. one or more d/t tools 70, 75, 76, 79, and
h. an access tube 86;

The outer sac 62 is a malleable sac comprising at least one malleable segment 90 that can expand and/or conform, e.g. into a smaller passageway or cavity such as diverticulum 89. A railed diagnostic tool such as ultrasound device 70 can then be used to scan the diverticulum for irregularities. As an addition or alternative to the diagnostic tool, a railed therapeutic tool such as ablation tool 71 can be used to treat tissue at a target site within the diverticululm.

In addition or as an alternative to a malleable segment 90, a smaller passageway or cavity such as diverticulum 88 can be expanded into by an evaginating portion 78 of an inner sac 77 that exits the outer sac 62 through a port 64 (e.g. valve). The diverticulum 88 can be inspected or treated by d/t tool 79 (e.g. ultrasound probe or ablation tool (e.g. RF ablation tool)) that is housed by or attached to the inner sac 77. Inner sac 77 can be filled with a fluid (e.g. viscous fluid) to impart volume or expansion of inner sac 77 into diverticulum 88. Optionally, inner sac 77 is a malleable sac.

In addition or as an alternative to malleable segment 90 or port 64 with inner sac 77, the device can comprise a port 63 (e.g. valve) sized to allow passage of a robotic tool such as a therapeutic tool 75 (e.g. snare) for treating a polyp 91 or other target tissue. If the therapeutic tool 75 is a railed device, the port can be positioned in proximity to the rail. As depicted in FIG. 12a and FIG. 12e, the expandable device optionally comprise light sources such as railed light 101 (e.g. for illuminating the lumen of the sac 62) shown near the end of the rail 100 and/or a sac wall-embedded light 85 (e.g. for illuminating the target site). The expandable device can also comprise a camera such as railed camera 76 for visualization during the procedure.

The expandable device can optionally comprise an inner lumen 80 for transporting robots 82 or other tools. The inner lumen 80 can be filled with a cushioning fluid (e.g. gel, liquid, or gas) to protect the tools 82 from the patient and vice-versa during transport. The tools 82 can be directly housed by the inner lumen 80 or can be in the lumen of a second inner sac 81, for example, to separate the tools from the cushioning fluid. Although not illustrated, the inner sacs 80,81 can comprise valves for transport of the tools 82 from the inner sacs when needed.

The expandable device can optionally comprise an expandable or budding segment 83, as depicted in FIG. 12a and FIG. 12c. Although the budding segment 83 can be configure in any manner (e.g. ductile segment, shape memory segment, etc), the segment is optionally configured as a looped segment 94. Before insertion into a patient, the looped segment 94 is looped and clipped using a clip 93, thereby reducing the surface area of outer sac 62. When desired, the clip 93 can be released (e.g. by heat) to allow the looped segment to expand, as depicted in FIG. 12c. Such a budding segment can be used to, for example, provide more surface area in the wall, expand the wall to bud out, or to provide curvature in the wall.

The rail 65 can optionally be provided as a network of interconnected rails 67, 68, 69. Additionally or alternatively, the rail 65 can be provided as an inflatable rail, as depicted in FIG. 12f. The inflatable rail is comprises a flexible conduit, the lumen of which can be filled with a fluid to impart turgidity to the rail. For example, the inflatable rail can be filled from an access tube 104 through an access tube connector 103. The inflatable rail allows the rail to be preconfigured in a flexible manner such that the expandable device can be easily transported in the patient. When movement of railed devices is needed, the inflatable rail can then be inflated to turgidity to form a functional rail system. If the rail is a network of rails, the inflatable rail can optionally be configured with a fork (branch) splitting an input rail 67 into output rails 68 and 69. A control circuit can optionally be provided to differentially fill various branches of the rail network to turgidity by diverting fluid from an input rail 67 to one of the output rails 68 and 69. As depicted in FIG. 12d, an examplary control circuit is a fluidic amplifier 66 comprising an input rail 67 (conduit) which flows into a feedback cavity 98 and then forks into output rails (conduits) 68, 69. The flow of fluid from input rail 67 is selectively diverted to either output rail 68,69 using control passages (fluid inputs) 96 and 97 in combination with flow vent 99. An example of such a fluidic amplifier is described in further detail U.S. Pat. No. 4,000,757 (Freeman).

The outer sac 62 optionally comprises traction members 83 such as protrusions or pods with filaments extending thereof on the outer wall of the sac. Such traction members can aid in movement of the expandable device through the body cavity.

The expandable device optionally comprises a housekeeping robot such as robot 87 that configures the expandable device as needed during a procedure. For example, as depicted in FIG. 12a and FIG. 12b, a walking robot 87 or other robot (e.g. microrobot) can be configured to move and/or connect certain components within the expandable device. Optionally, the expandable device comprise an access tube(s) 86 that can be selectively coupled to one or more components within the expandable device such as inner sac 77 or an inflatable rail. As depicted in FIG. 12b, the expandable device can comprise clips 88 or other attachment devices (e.g. magnet) for securing a component 92 (e.g. segment of an access tube 86 or tool) to a sac wall 62 until needed. When needed the robot 87 can retrieve the component 92 and move or couple the component to perform a desired function.

Example 12 Pleated Sac

FIG. 13 depicts a pleated configuration in an expandable sac (note that the FIG. 13 depicts pleats for illustrative purposes only and does not show an enclosed sac). The sac comprises a plurality of segments 129 connected by pleats 130. The pleats 130 provide preformed fold lines such that the sac can expand from a collapsed state, as depicted in FIG. 13a to an expanded state, as depicted in FIG. 13b. The segments 129 can be stiff segments or malleable segments. The pleats 130 are flexible and optionally malleable. The segments 129 and the pleats 130 can be made of the same material, e.g. where the pleats 130 are thinner-walled than the segments 129, or can be made from a different, more flexible material than the segments 129.

Example 13 Tethered Sac Wall

Figure 14A:
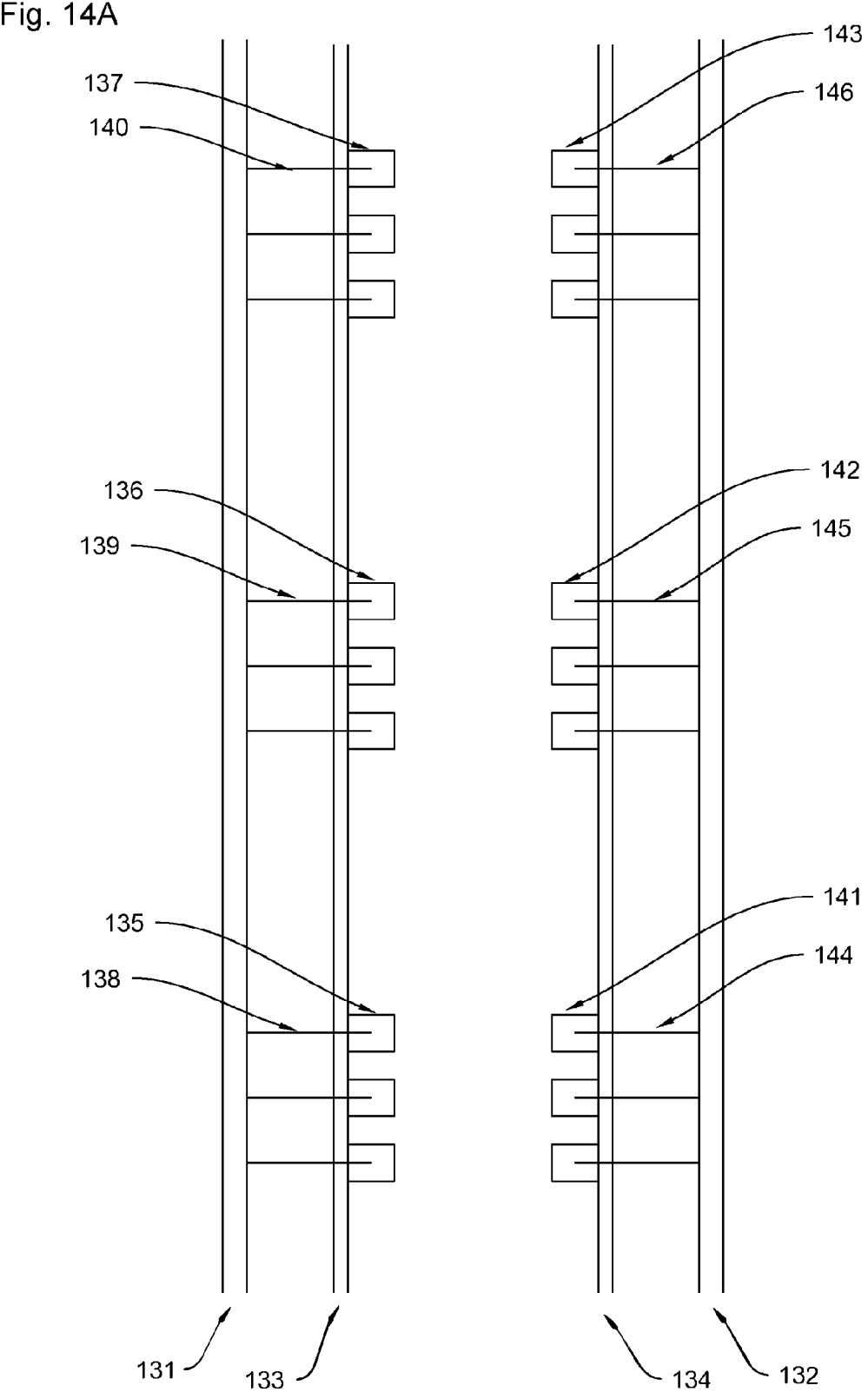
FIG. 14A through FIG. 14C depict motorized devices tethered to a sac wall.

FIG. 14 depicts an expandable sac wall tethered to a motorized device ('tethered motorcar'). As detailed herein, an expandable sac wall can be tethered to a motorized device (e.g. railed device) for movement of the sac wall. The expandable sac can comprise sac wall segments 131, 132 coupled to motorized devices such as railed devices 135, 136, 137, 141, 142, and 143 by tethers 138, 139, 140, 144, 145, and 146 respectively. The railed devices can move along rails 133, 134 to move (push or pull) the tethered segments of the expandable sac. The rails 133, 134 are optionally unattached (free) from the expandable sac wall or are attached to the sac wall at a location other than at segments 131, 132 to allow movement of the railed devices and tethered segments about the rails.

In one embodiment, a plurality of tethered motorized devices can be used to impart a bend or curvature in the sac by spreading or condensing a segment of the wall.

For example, the motorized devices can be used to transition the sac from a natural state (FIG. 14*a*) to a curved state (FIG. 14*b*) by moving the tethered wall segments on one wall closure to each other and/or moving tethered wall segments another wall further apart.

Figure 14B:
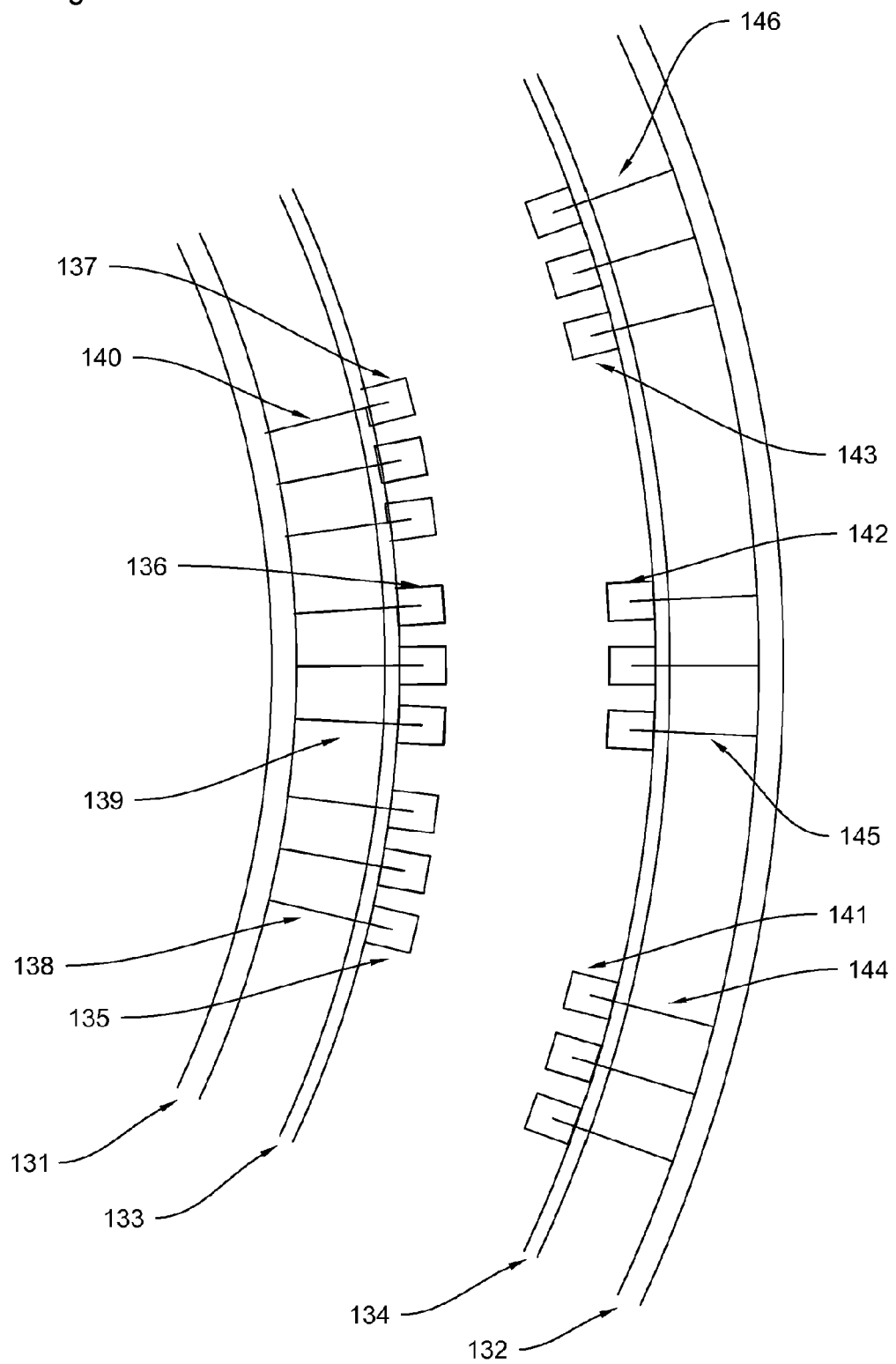
Figure 14C:
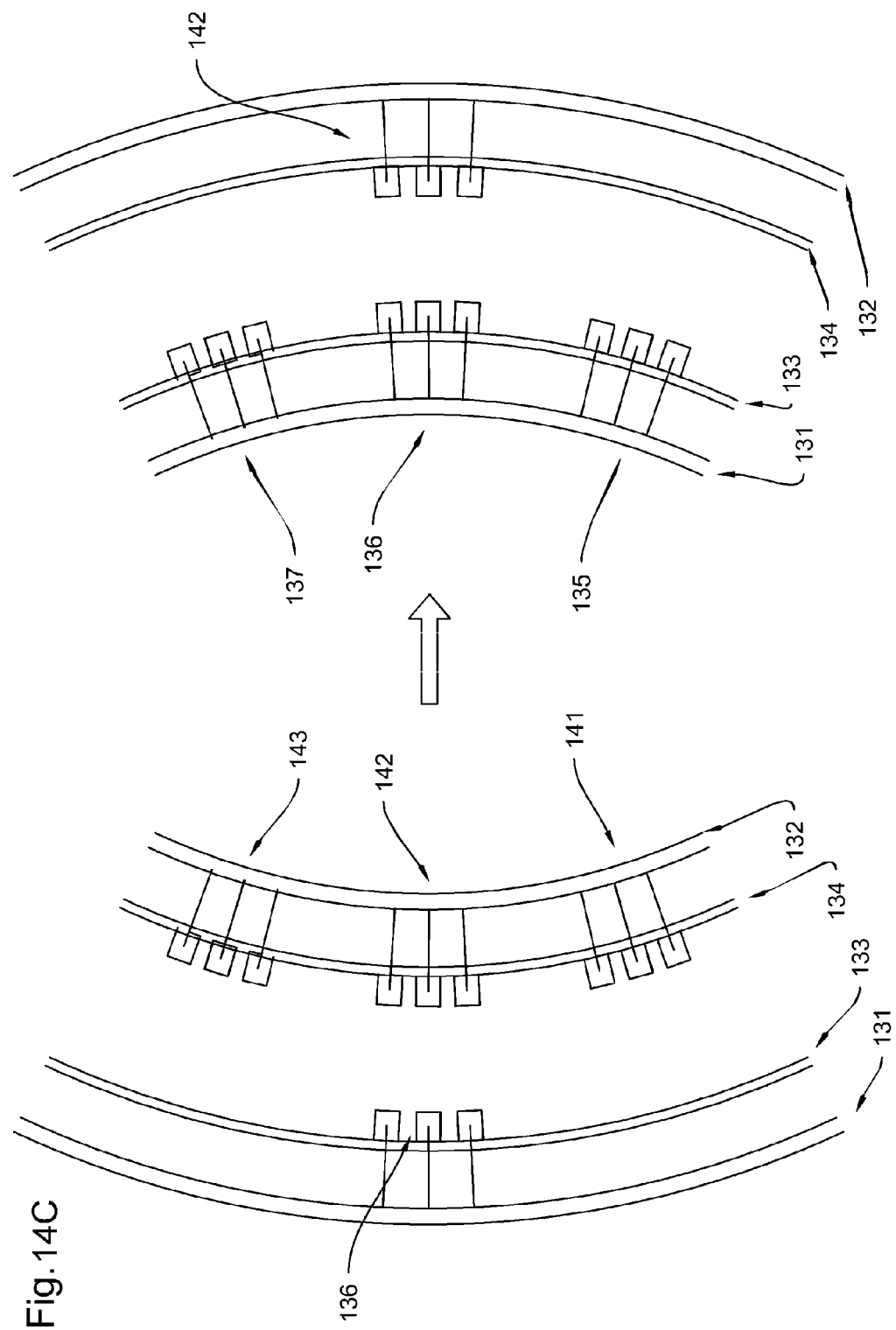

In FIG. 14*b*, the motorized devices 135, 136, 137 on rail 133 (shown on the left side) have been moved closure to each other, thereby imparting a curve to the left. The sac wall can be induced to curve right by moving the motorized devices 141, 142, 143 on rail 134 (shown on right side) closure to each other. Depending on the configuration of the wall segment and location of tethering, a given wall can be induced to curve either way upon moving the motorized devices closure to each other (or further apart). For example, FIG. 14*c* depicts sac walls that curve towards the rail as the motorized devices are condensed. Such a configuration can mimic, for example, the manner in which a bicep muscle induces an arm to articulate at the elbow.

Although curved bends are depicted in the figures, the expandable device can also be configured to articulate (as in a joint or hinge) if the two or more motorized devices are tethered to more rigid segments connected by a pleat.

Such bending or curvature is useful, for example, as the expandable device travels through a curved body cavity or lumen (e.g. colon) or contours against a curved organ or other target site.

Another useful movement imparted by such a configuration is provided by repeatedly alternating the curved wall (alternating between left and right bending) to provide a "wiggling" action of the expandable sac. A wiggling action can be used to gently maneuver burrow a sac into or through a small passageway or in between two organs.

In addition to imparting curvature, the motorized rail cars can be used to move the expandable device globally (e.g. pulling rear segments of the expandable device forward and repeating) or to spread the expandable device out (e.g. pulling segments along a plurality of axes simultaneously).

Example 14 Fragmented Tool

Figure 15:
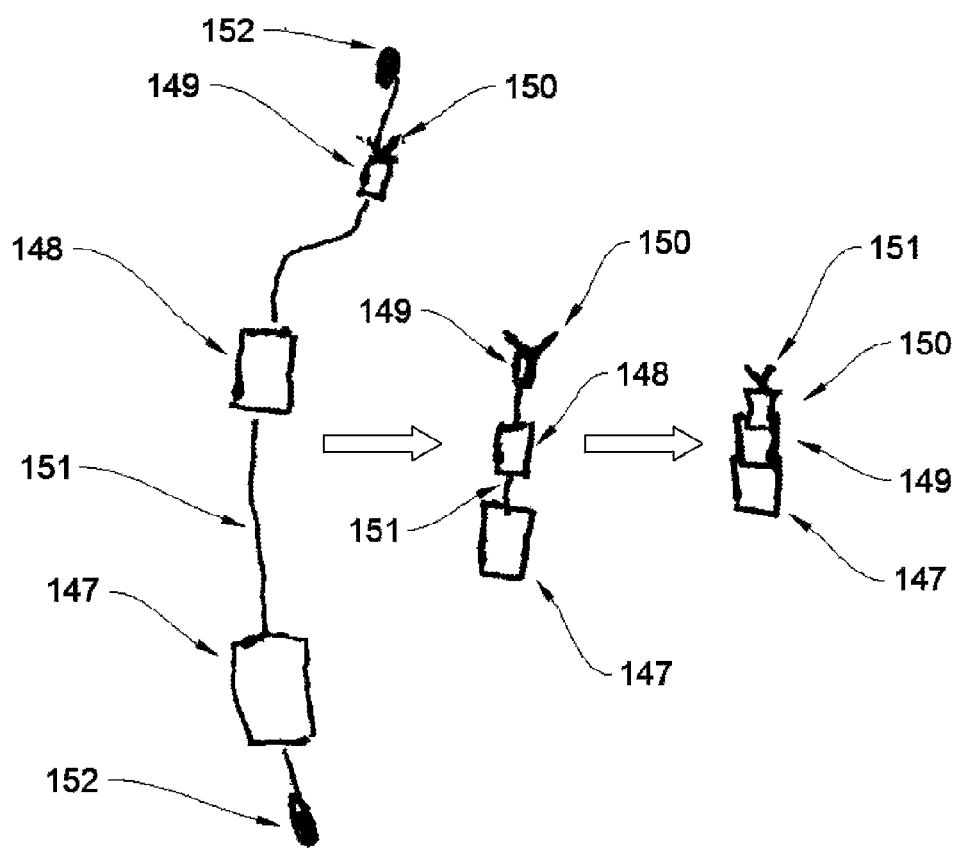
FIG. 15 depicts a fragmented tool.

FIG. 15 depicts a fragmented tool useful in an expandable device of the invention. The tool comprises fragments 147, 148, and 149 threaded on a pull string 151. The pull string 151 can be anchored to one of the terminal fragments 147, 149 comprises a hook, ball, or other member 152 for coupling to one terminal fragment as the string is pulled through the other terminal fragment. For example, to assemble the fragments 147, 148, 149, the terminal fragment 147 is stabilized (e.g. held in place) while the string 151 is pulled through the terminal fragment 147. As the string 151 is pulled, it brings fragment 149 and 148 into contact with fragment 147. Once in the correct orientation, the fragments 147, 148, 149 are coupled together to form a functional tool. For example, the ends of each fragment can have clips or locking members that couple to each other as the string is pulled to tension. The fragmented tool can be, for example, a robot with a d/t instrument such as forceps 150.

A fragmented tool allows the tool to be provided in a collapsed and/or more flexible configuration while it is transported to a target site in a body cavity.

Example 15 Method of Using an Expandable Device

An expandable device of the present invention is provided.

The device comprises an outer sac comprising:
a. a rail system comprising a rail and railed devices comprising motors (motorized railed devices such as inchworm-type motors);
b. one or more light sources;
c. one or more valves to allow protrusion of devices (e.g. d/t devices) outside the sac when needed but prevent backward reflux into the lumen of the sac while when the device is withdrawn/retracted back inside the sac;
d. a small camera attached to the inner wall at the distal end;
e. an access tube at the proximal end of the sac (used to transport fluids and/or devices into or out of the sac); and
f. irregular small structures or other traction members (e.g. protrusions) on the external wall of the sac to permit better traction with the body cavity wall.

The expandable device further comprises a first inner sac in the lumen of the outer sac. Like the outer sac, the inner sac has a rail system, light sources, valves, and a camera.

In the inner of the first inner sac is a second inner sac, also comprising a rail system, light sources, valves, and a camera.

The outer and/or inner sacs can comprise d/t tools (e.g. robot tools) for performing desired functions.

Through the access tube, fluids and/or devices (e.g. robots) can be injected and withdrawn from the sac. In this configuration, the access tube is initially attached to the outer sac, for example, through a reversible coupler; however, the inner sacs can comprise couplers for connecting to the access tube. The inner sacs can couple to the access tube by maneuvering into position (e.g. using railed devices tethered to the wall of the respective sac allowing a segmental crawling motion of any of the sacs). Additionally or alternatively, a robot (e.g. walking robot) can be used to couple/uncouple sacs from the access tube, e.g. as detailed in Example 11.

The expandable device is inserted into the patient by pushing the device through the rectum into the colon manually using a rectal speculum. During insertion, the expandable device is in a collapsed state. The sacs are flexible (e.g. malleable) such that the can be folded, rolled, or otherwise collapsed such that the expandable device has a minimal cross section. Once inside the colon, any gases or other fluids needed to expand one or more sacs can be injected through the access which is to be connected to the appropriate sac(s). Expulsion of the expandable device can occur, for example, by normal defecation, but if needed can be pulled out of the rectum manually.

D/t tools (e.g. robots or other tools) which are to function within the expandable device can be folded within the sac(s) if they are small enough or flexible enough to fit through the rectum while inside the expandable device. For instance, the tools needed to function within a sac (e.g. the second inner sac) can be placed into the correct sac while it is still visible outside the rectum and then complete the pushing of the entire expandable device or configuration of sacs through the rectum. However, the tools can also be inserted into the lumen of sacs through the access tube once the expandable device has been inserted. In this manner, the tools can be individually pushed through the rectum.

Once launched into the colon, the expandable device can move through the colon by any means, for example, by motorized devices tethered to the wall of the outer sac and/or by retroperistalsis (e.g. using electrode-induced or muscle contraction or other induced contraction or by voluntary muscle contractions)

The first inner sac can be expanded to a desired volume with gas or other fluid to allow the colonic wall to contract around the entire expandable device and propel it up the colon in retroperistalsis in addition to the movement imparted to the expandable device by the motorized railed devices moving along the rail of the outermost sac. In this manner, the expandable device travels to the target location with a camera for visual guidance.

To perform a clinical procedure, once the expandable device arrives at the target site, one or more tools are transported to the appropriate location within the expandable device. In one embodiment, a small ultrasound probe can be used to image the body cavity by localizing the probe against a sac wall which is in contiguity with the colonic wall at the target location. For example, the probe is initially coupled to a rail on the luminal wall of the second inner sac and then is transported along the rail to the site of a lesion in the colon. The second inner sac can also be configured for segmental movement of its wall tethered to a railed device until the probe it is aligned closely to the target location at the colonic wall. Hence, the ultrasound probe is now adjacent to the target location separated by the three walls of the three sacs. At this point, the ultrasound probe is activated and scans the wall adjacent to the lesion to image the colonic wall. Depending upon the interpretation of the ultrasound images which are transmitted by the probe through radio waves, the user of the expandable device can deploy a therapeutic tool (e.g. cryogenic ablation tool), for example, through the access tube, then positioning the therapeutic tool alongside the ultrasound probe at the target site. The therapeutic tool is then activated, for example, by releasing a premeasured liquid inside the tool which cools it down to a desired temperature thus decreasing the temperature of the adjacent walls of the three sacs such that the lesion which touches the outer surface of the outermost sac becomes frozen and sloughs off.

Alternately, if the device and method chosen to obliterate the lesion requires direct contact with the lesion on the colonic wall (e.g. cutting tool, laser, or RF therapy), a different therapeutic tool can be transported to the periphery of the outer sac wall through ports in the sac wall. If the tool is housed in an inner sac (e.g. second inner sac), the ports in each of the sacs are aligned to allow passage of the tool from the inner sac to the periphery of the outer sac. The tool can be maneuvered though the ports using, for example, using a telescoping arm (or other robotic arm) that extends through the aligned ports to the lesion at the periphery of the outer sac. After treating the lesion, the robotic arm is withdrawn through the three ports. The ports can be configured as self-sealing valves such that they close upon the robot arm retracting back through the ports.

We claim:

1. An expandable device comprising:
   a. a sac comprising a lumen, wherein the sac is expandable;
   b. a rail in the lumen of the sac; and
   c. a railed device coupled to the rail for movement thereon;
   wherein:
      the rail comprises a conduit made from a flexible material;
      the conduit comprises an inlet configured for receiving a fluid to fill the conduit or allow the fluid to flow through the conduit;
      when not filled with the fluid or when not having the fluid flow there through, the conduit is flexible or flaccid; and
      when filled with the fluid or when having the fluid flow there through, the conduit:
         i. is turgid relative to when the conduit is flexible or flaccid;
         ii. supports the railed device; and
         iii. guides the railed device for movement along the conduit.

2. The expandable device of claim 1, wherein the rail is mounted to a luminal wall of the sac, embedded in the luminal wall of the sac, or contoured along the luminal wall of the sac.

3. The expandable device of claim 1, further comprising a motor for providing said movement of the railed device.

4. The expandable device of claim 1, further comprising sensors on the sac.

5. The expandable device of claim 1, further comprising an access tube in fluid connection with the sac.

6. The expandable device of claim 1, wherein the sac is configured for expansion by fluid pressure.

7. The expandable device of claim 1, wherein the railed device is tethered to the sac, whereby the sac or a portion thereof can be moved by moving the railed device.

8. The expandable device of claim 1, wherein the sac is malleable.

9. The expandable device of claim 8, wherein the sac is transparent.

10. The expandable device of claim 8, wherein the sac comprises a plurality of wall segments with different malleability.

11. The expandable device of claim 10, wherein the sac comprises a thermoplastic resin, wherein the sac is malleable at a physiologically acceptable temperature.

12. The expandable device of claim 1, wherein the sac comprises a port connecting the lumen of the sac with a periphery of the sac.

13. The expandable device of claim 1, further comprising a fork in the conduit, wherein the fork branches a first conduit into a plurality of conduits, wherein each of the plurality of conduits can support a railed device when turgid.

14. The expandable device of claim 13, wherein the fork comprises a control circuit configured to differentially control the flow of the fluid from the first conduit into the plurality of conduits.

15. The expandable device of claim 14, wherein the control circuit is a fluidic amplifier.

16. The expandable device of claim 1, wherein:
   a. the conduit is embedded in the sac or contoured along a luminal wall of the sac; and
   b. the conduit provides a framework for the sac, whereby filling the conduit with the fluid or flowing the fluid through the conduit provides rigidity to the sac or expands the sac or a portion of the sac.

17. The expandable device of claim 16, wherein the sac comprises a first portion and a second portion, and wherein the conduit is localized to the first portion of the sac and configured such that filling the conduit with the fluid or flowing the fluid through the conduit:
  a. expands the first portion of the sac or provides rigidity to the first portion of the sac; and
  b. does not expand the second portion of the sac or does not provide rigidity to the second portion of the sac.

18. The expandable device of claim 16, wherein:
  a. the sac wall is rigid when the conduit is turgid; and
  b. the sac wall is flexible when the conduit is flexible or flaccid.

19. An expandable device comprising:
  a. a sac comprising a lumen, wherein the sac comprises a first portion and a second portion, and wherein the sac is expandable; and
  b. a tool in the lumen of the sac; and
  c. a framework comprising a conduit embedded in the sac or attached to the sac, wherein:
    i. the conduit is configured to receive a fluid to fill the conduit or allow the fluid to flow through the conduit;
    ii. the conduit is localized to the first portion of the sac;
    iii. when not filled with the fluid or when not having the fluid flow there through, the conduit is flexible or flaccid; and
    iv. when filled with the fluid or when having the fluid flow there through, the conduit is: turgid relative to when not filled with the fluid or when not having the fluid flow there through, and configured to expand the first portion of the sac and not expand the second portion of the sac.

20. The expandable device of claim 19, further comprising a railed device, wherein, when filled with the fluid or when having the fluid flow there through, the conduit provides a rail for the railed device to support the railed device and guide the railed device for movement along the conduit.

* * * * *